United States Patent
Holdgrün et al.

(10) Patent No.: US 6,482,947 B1
(45) Date of Patent: Nov. 19, 2002

(54) SUBSTITUTED (HETERO) ARYL COMPOUNDS, PROCESS FOR THEIR PREPARATION, AGENTS CONTAINING THEM AND THEIR USE AS SAFENERS

(75) Inventors: Xenia Holdgrün, Kriftel/Ts.; Lothar Willms, Hillscheid; Klaus Bauer, Hanau; Klaus Trinks, Flörsheim am Main; Hermann Bieringer, Eppstein/Ts., all of (DE)

(73) Assignee: Hoechst Aktiengesellschaft, Frankfurt (DE)

( * ) Notice: Subject to any disclaimer, the term of this patent is extended or adjusted under 35 U.S.C. 154(b) by 0 days.

(21) Appl. No.: 09/015,642

(22) Filed: Jan. 29, 1998

Related U.S. Application Data

(62) Division of application No. 08/440,886, filed on May 15, 1995, now Pat. No. 5,739,079, which is a continuation of application No. 08/099,068, filed on Jul. 29, 1993, now abandoned.

(30) Foreign Application Priority Data

Aug. 1, 1992 (DE) .......................................... 42 25 493

(51) Int. Cl.$^7$ .......................................... C07D 239/545
(52) U.S. Cl. ...................... 544/239; 544/319; 544/468; 546/178; 546/301; 548/187; 548/228; 548/229; 548/544; 549/66; 549/479
(58) Field of Search .............................. 544/239, 319, 544/468; 546/178, 301; 548/187, 228, 229, 544; 549/66, 479

(56) References Cited

U.S. PATENT DOCUMENTS

| | | | | |
|---|---|---|---|---|
| 3,928,602 A | 12/1975 | Barthold et al. | ............ | 424/308 |
| 4,067,725 A | 1/1978 | Schurter et al. | ................ | 71/94 |
| 4,115,100 A | * 9/1978 | Schurter et al. | ................ | 71/22 |
| 4,414,020 A | 11/1983 | Heier et al. | ..................... | 71/108 |
| 4,416,687 A | 11/1983 | D'Amico et al. | ............. | 71/109 |
| 4,602,932 A | 7/1986 | Handte et al. | ................. | 71/88 |
| 4,623,727 A | 11/1986 | Hübele | ........................ | 546/178 |
| 4,902,340 A | 2/1990 | Hübele | ........................... | 71/94 |
| 5,030,269 A | 7/1991 | Barton et al. | .................. | 71/88 |

FOREIGN PATENT DOCUMENTS

| | | |
|---|---|---|
| CA | 1259200 | 2/1989 |
| DE | 26 37 886 | 3/1977 |
| EP | 0031938 | 7/1981 |
| EP | 0086750 | 8/1983 |
| EP | 0088066 | 9/1983 |
| EP | 0094349 | 11/1983 |
| EP | 0112799 | 7/1984 |
| EP | 0154153 | 9/1985 |
| EP | 0170906 | 2/1986 |
| EP | 0293062 | 11/1988 |
| FR | 1465584 | 11/1965 |
| ZA | 839030 | 5/1983 |

OTHER PUBLICATIONS

Babichev et al., Chemical Abstracts, vol. 62:1766c, 1960.*
Safonova et al., Chemical Abstracts, vol. 74:141668, 1971.*
Dahm et al., Chemical Abstracts, vol. 78:84397, 1973.*
Bertrand et al., Chemical Abstracts, vol. 80:37020, 1974.*
Myshkina et al., Chemical Abstracts, vol. 83:9982, 1975.*
Schurter et al., Chemical Abstracts, vol. 86:189735, 1977.*
Arakawa et al., Chemical Abstracts, vol. 87:23191, 1977.*
Singh et al., Chemical Abstracts, vol. 92:215321, 1980.*
Sashi et al., Chemical Abstracts, vol. 97:38586, 1982.*
Yokoyama, Chemical Abstracts, vol. 101:211137, 1084.*
Guy et al., Chemical Abstracts, vol. 107:236585, 1987.*
Curran et al., Chemical Abstracts, vol. 110:172451, 1989.*
Baldwin et al., Chemical Abstracts, vol. 117:69850, 1992.*
Hafez et al., Chemical Abstracts, vol. 212, abstract 108644, 1994.*
Harada et al., Chemical Abstracts, vol. 117, abstract 48615, 1992.*
Kita et al., Chemical Abstracts, vol. 115, abstract 102709, 1991.*
Astles et al., Chemical Abstracts, vol. 114, abstract 185569, 1991.*
Nawamaki et al., Chemical Abstracts, vol. 110, abstract 95226, 1989.
Nakamura et al., Chemical Abstracts, vol. 109, abstract 73852, 1988.
Budesinsky et al., Chemical Abstracts, vol. 96, abstract 35187, 1982.
Abdalla et al., Chemical Abstracts, vol. 90, abstract 137633, 1979.
Frei et al., Chemical Abstracts, vol. 76, abstract 14329, 1972.*

* cited by examiner

Primary Examiner—Richard L. Raymond
(74) Attorney, Agent, or Firm—Frommer Lawrence & Haug LLP

(57) ABSTRACT

Compounds of the formula I and their salts, as defined in claim 1, are suitable as safeners for protecting crop plants against the phytotoxic side-effects of herbicides.

13 Claims, No Drawings

SUBSTITUTED (HETERO) ARYL COMPOUNDS, PROCESS FOR THEIR PREPARATION, AGENTS CONTAINING THEM AND THEIR USE AS SAFENERS

This application is a divisional of U.S. application Ser. No. 08/440,886, filed May 15, 1995, now issued as U.S. Pat. No. 5,739,079, which in turn is a continuation of U.S. application Ser. No. 08/099,068, filed Jul. 29, 1993, now abandoned.

The invention relates to the technical area of crop-protection agents, in particular active ingredient/antidote combinations, which are highly suitable for use against competing weeds in crops of useful plants.

Use of crop treatment agents, in particular use of herbicides, can result in undesired damage to the treated crop plants. Many herbicides are not fully compatible (selective) with some important crop plants, such as corn, rice or cereals, so that their use is very restricted. They can therefore sometimes not be employed at all or only at such low application rates that the desired broad herbicidal activity against the weeds is not ensured. Thus, for example, many herbicides of the substance classes (A) mentioned below cannot be employed sufficiently selectively in corn, rice or in cereals. In particular in the case of post-emergence application of herbicides, phytotoxic side-effects on the crop plants occur, and it is desired to prevent or reduce this phytotoxicity.

It has already been disclosed to employ herbicides in combination with compounds which reduce the phytotoxicity of herbicides in crop plants without correspondingly reducing the herbicidal activity against the weeds. Such combination partners are known as "safeners" or "antidotes".

EP-A-31 938 discloses the use of aryloxycarbonitriles and aryloxycarboxamide oximes as safeners for herbicides from the series consisting of the phenoxyphenoxycarboxylic esters, chloroacetanilides and dimedone derivatives. EP-A-170 906 describes, inter alia, phenoxycarboxylic ester oximes and EP-A-154 153 describes aryloxy compounds as safeners for phenoxyphenoxy and heteroaryloxyphenoxy herbicides.

EP-A-112 799 mentions 4-chlorophenoxy- and 4-chloro-2-mnethylphenoxyacetic acid as safeners for propargyl 2-[4-(3, 5-dichloropyridyl-2-oxy)phenoxy]propionate.

EP-A-293 062 describes the use of aryloxy compounds as safeners for cyclohexanedione herbicides, and EP-A-88 066 the use of 3,5-bis(trifluoromethyl)phenoxycarboxylic acid derivatives as safeners, in particular for acetamides, specifically for triallate.

EP-A-86 750 describes quinoline-8-oxyalkanecarbornitriles and quinoline-8-oxyalkanecarboxamide oximes as safeners for phenoxyphenoxyalkanecarboxylic esters and sulfonyl ureas. EP-A-94 349 discloses the use of corresponding carboxylic esters as safeners for herbicides from various structural classes.

DE 2637886 has already disclosed the use of 3-pyridyloxyalkanecarboxamides as safeners for herbicides from the triazine, carbamate and haloacetanilide series.

It has now been found that, surprisingly, a group of aryl and heteroaryl derivatives of the formula I below is highly suitable for protecting crop plants against the harmful effects of aggressive agrochemicals, in particular herbicides.

Aryl and heteroaryl derivatives which are suitable for protecting crop plants against the harmful effects of aggressive agrochemicals conform to the formula I

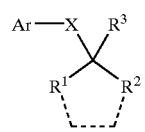
(I)

in which
R$^1$ and R$^2$, independently of one another, are radicals of the formula

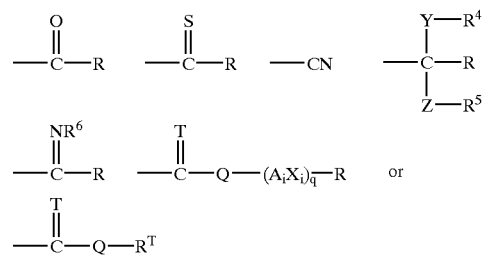

in which R, R$^T$, R$^4$, R$^5$, R$^6$, Y, T, Z, Q, A$_i$, X$_i$ and q are as defined below, or R$^1$ and R$^2$ are bonded to one another and together are a group of the formula

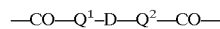

in which
Q$^1$ and Q$^2$, independently of one another, are as defined for Q and
D is a divalent group of the formula CR'R" or C=O, where R' and R", independently of one another, are hydrogen or C$_1$–C$_4$-alkyl, R$^3$ is hydrogen, halogen, C$_1$–C$_{18}$-alkyl, C$_2$–C$_8$-alkenyl, C$_2$–C$_8$-alkynyl, C$_1$–C$_{18}$-alkoxy, C$_2$–C$_8$-alkenyloxy, C$_2$–C$_8$-alkynyloxy, C$_1$–C$_{18}$-alkylthio, C$_2$–C$_8$-alkenylthio, C$_2$–C$_8$-alkynylthio, where each of the 9 last-mentioned radicals is in each case unsubstituted or substituted by one or more radicals from the group consisting of halogen, nitro and cyano, or is C$_3$–C$_{12}$-cycloalkyl which is unsubstituted or substituted by one or more radicals from the group consisting of C$_1$–C$_4$-alkyl, halogen, nitro and cyano, or is SiR$^a$R$^b$R$^c$, in which R$^a$, R$^b$ and R$^c$, independently of one another, are C$_1$–C$_4$-alkyl, C$_2$–C$_4$-alkenyl, C$_2$–C$_4$-alkynyl or substituted or unsubstituted phenyl, or is a radical of the formula Ar'X'—, in which Ar' and X' are defined analogously to Ar and X, X is O, S, NH—NH or NR$^d$, where R$^d$ is defined analogously to R$^4$, or is —CH$_2$O—, —CH$_2$S—, —CH(Ar)O— or —CH(Ar)S—, Ar is an aromatic radical, for example an unsubstituted or substituted phenyl, naphthyl or heteroaryl radical, preferably a carbocyclic or carbobicyclic radical of the formula

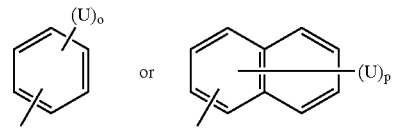

in which (U) are identical or different radicals which, independently of one another, are hydrogen, halogen, cyano, nitro, amino or $C_1-C_8$-haloalkyl, $C_1-C_8$-haloalkoxy, $C_1-C_8$-alkyl, $C_1-C_8$-alkoxy, mono-$(C_1-C_4$-alkyl) amino, di-$(C_1-C_4$-alkyl)amino, $C_1-C_9$-alkylthio or $C_1-C_8$-alkylsulfonyl, where each of the 8 last-mentioned radicals is unsubstituted or substituted by one or more, preferably up to three identical or different substituents from the group consisting of halogen, $C_1-C_8$-haloalkoxy, nitro, cyano, hydroxyl, $C_1-C_8$-alkoxy, in which one or more, preferably up to three, $CH_2$ groups may be replaced by oxygen, $C_1-C_8$-alkylthio, $C_1-C_6$-alkylsulfinyl, $C_1-C_6$-alkylsulfonyl, $C_2-C_8$-alkenylthio, $C_2-C_8$-alkynylthio, $C_2-C_8$-alkenyloxy, $C_2-C_8$-alkynyloxy, $C_3-C_7$-cycloalkyl, $C_3-C_7$-cycloalkoxy, mono- and di-$(C_1-C_4$-alkyl)amino and $C_1-C_8$-alkoxycarbonyl, and preferably hydrogen, halogen, $C_1-C6$-haloalkyl, such as trifluoromethyl, $C_1-C_6$-haloalkoxy, such as difluoromethoxy, $C_1-C_6$-alkyl, $C_1-C_6$-alkoxy, $C_1-C_6$-alkythio, $C_1-C_6$-alkylsulfonyl, nitro, amino, $(C_1-C_2$-alkyl) amino, di-$(C_1-C_2$-alkyl) amino or cyano, and o is an integer from 1 to 5, preferably from 1 to 3, and
p is an integer from 1 to 7, preferably from 1 to 3, or Ar is a monocyclic or bicyclic heteroaryl radical from the group consisting of furyl, thienyl, pyrrolyl, pyrazolyl, thiazolyl, oxazolyl, pyridinyl, pyrimidinyl, pyrazinyl, pyridazinyl and quinolinyl, each of which is unsubstituted or substituted by one or more, preferably from one to three, of said radicals U, R is hydrogen or an aliphatic, aromatic, heteroaromatic, araliphatic or heteroaraliphatic radical having 1 to 30 carbon atoms and, if desired, containing one or more functional groups, for example R is a hydrogen, $C_1-C_{18}$-alkyl, $C_3-C_{12}$-cycloalkyl, $C_2-C_8$-alkenyl, $C_2-C_8$-alkynyl, heterocyclyl, phenyl or heteroaryl radical, where each of the above C-containing radicals, independently of one another, is unsubstituted or substituted by one or more radicals from the group consisting of halogen, cyano, thio, nitro, hydroxyl, $C_1-C_8$-alkyl, the latter only in the case of cyclic radicals, $C_1-C_8$-haloalkyl, $C_2-C_8$-alkoxy, $C_2-C_8$-alkenyloxy, $C_2-C_8$-alkynyloxy, $C_1-C_8$-haloalkoxy, $C_2-C_8$-alkylthio, $C_2-C_9$-alkenylthio, $C_2-C_8$-alkynylthio, $C_3-C_7$-cycloalkyl, $C_3-C_7$-cycloalkoxy, radicals of the formulae -NR*R** and —CO—NR*R** and —O—CO—NR*R**, where R* and R** in the three last-mentioned radicals are, independently of one another, hydrogen, $C_2-C_8$-alkyl, $C_2-C_8$-alkenyl, $C_2-C_8$-alkynyl, benzyl, phenyl or substituted phenyl, or together with the nitrogen atom are a 3- to 8-membered heterocyclic ring which may contain up to 2 further heteroatoms from the group consisting of N, O and S, and may be substituted by $C_1-C_4$-alkyl, and $(C_1-C_8$-alkoxy)carbonyl, $(C_1-C_8$-alkoxy)thiocarbonyl, $(C_2-C_8$-alkenyloxy) carbonyl, $(C_1-C_8$-alkylthio)carbonyl, $(C_2-C_8$-alkenylthio)carbonyl, $(C_2-C_8$-alkynylthio)carbonyl, $(C_2-C_8$-alkynyloxy carbonyl, formyl, $(C_1-C_8$-alkyl) carbonyl, $(C_2-C_8$-alkenyl) carbonyl, $(C_2-C_8$-alkynyl)carbonyl, $C_1-C_4$-alkylimino, $C_1-C_4$-alkoxyimino, $(C_1-C_8$-alkyl) carbonylamino, $(C_2-C_8$-alkenyl) carbonylamino, $(C_2-C_8$-alkynyl) carbonylamino, $(C_1-C_8$-alkoxy)carbonylamino, $(C_2-C_8$-alkenyloxy) carbonylamino, $(C_2-C_8$-alkynyloxy)carbonylamino, $(C_1-C_8$-alkyl) aminocarbonylamino, $(C_1-C_6$-alkyl)carbonyloxy, which is unsubstituted or substituted by halogen, $NO_2$, $C_1-C_4$-alkoxy or substituted or unsubstituted phenyl, $(C_2-C_6$-alkenyl)carbonyloxy, $(C_2-C_6$-alkynyl)carbonyloxy, $(C_1-C_8$-alkoxy)carbonyloxy, $(C_2-C_8$-alkenyloxy)carbonyloxy, $(C_2-C_6$-alkynyloxy)carbonyloxy, $C_1-C_8$-alkylsulfonyl, phenyl, phenyl-$C_1-C_6$-alkoxy, phenyl-$(C_1-C_6$-alkoxy) carbonyl, phenoxy, phenoxy-$C_1-C_6$-alkoxy, phenoxy-$(C_1-C_6$-alkoxy) carbonyl, phenoxycarbonyl, phenylcarbonyloxy, phenylcarbonylamino, phenyl-$(C_1-C6$-alkyl) carbonylamino and phenyl-$(C_1-C_6$-alkyl) carbonyloxy, where the 11 last-mentioned radicals are unsubstituted or substituted on the phenyl ring by one or more radicals from the group consisting of halogen, $C_1-C_4$-alkyl, $C_1-C_4$-alkoxy, $C_1-C_4$-haloalkyl, $C_1-C_4$-haloalkoxy and nitro, and radicals of the formulae —SiR'$_3$, —O—SiR'$_3$, (R')$_3$Si—$C_1-C_6$-alkoxy, —CO—O—NR'$_2$, —O—N=CR'$_2$, —N=CR'$_2$, —O—NR'$_2$, —CH(OR')$_2$, and —O—(CH$_2$)$_m$—CH(OR')$_2$, in which the R' in said formulae is, independently of one another, hydrogen, $C_1-C_4$-alkyl or phenyl, which is unsubstituted or monosubstituted or polysubstituted by radicals from the group consisting of halogen, $C_1-C_4$-alkyl, $C_1-C_4$-alkoxy, $C_1-C_4$-haloalkyl, $C_1-C_4$-haloalkoxy and nitro, or in pairs are a $C_2-C_6$-alkylene chain and m=0 to 6, or a substituted alkoxy radical of the formula R"O—CHR'"CH(OR")—$C_1-C_6$-alkyl, in which the R", independently of one another, are $C_1-C_4$-alkyl or together are a $C_1-C_1$-alkylene group, and R'" is hydrogen or $C_1-C_4$-alkyl, $R^T$ is a radical of the formula —CO—R, —CS—R, —NR$^f$R$^g$, —N=CR$^h$R$^i$ or SiR$^a$R$^b$R$^c$, where R is as defined above, and R$^f$, R$^g$, R$^h$ and R$^i$, independently of one another are hydrogen, $C_1-C_4$-alkyl, $C_2-C_4$-alkenyl, $C_2-C^4$-alkynyl, benzyl, phenyl or substituted phenyl, or R$^f$ and R$^g$ together with the nitrogen atom are a 5- or 6-membered heterocyclic ring which may contain up to 2 further heteroatoms from the group consisting of N, O and S, and which may be substituted by $C_1-C_4$-alkyl, and R$^a$, R$^b$ and R$^c$, independently of one another, are $C_1-C_4$-alkyl, $C_2-C_4$-alkenyl, $C_2-C_4$-alkynyl, phenyl or substituted phenyl, Y and Z, independently of one another, are oxygen, sulfur in its various oxidation states, preferably S, SO or $SO_2$, or —NR$^e$, where R$^e$ is defined analogously to R$^4$, $R^4$ and $R^5$ are identical or different and, independently of one another, are hydrogen, $C_1-C_6$-alkyl, $C_2-C_6$-alkenyl, $C_2-C_6$-alkynyl, $(C_1-C^6$-alkyl)carbonyl, where, each of the 4 last-mentioned radicals is unsubstituted or substituted by one or more substituents from the group consisting of halogen, $C_1-C_4$-haloalkoxy, nitro, cyano, hydroxyl, $C_1-C_8$-alkoxy and $C_1-C_8$-alkoxy, in which one or more, preferably up to three, $CH_2$ groups which are not bonded directly to one another are replaced by oxygen, and $C_1-C_8$-alkylthio, $C_1-C_8$-alkylsulfonyl, $C_2-C_8$-alkenylthio, $C_2-C_8$-alkynylthio, $C_2-C_8$-alkenyloxy, $C_2-C_8$-alkynyloxy, $C_3-C_7$-cycloalkyl, $C_3-C_7$-cycloalkoxy and amino, mono- and di-$(C_1-C_4$-alkyl) amino, or are formyl, SiR$^a$R$^b$R$^c$, in which R$^a$, R$^b$ and R$^c$, independently of one another, are $C_1-C_4$-alkyl, $C_2-C_4$-alkenyl, $C_2-C_4$-alkynyl or substituted or unsubstituted phenyl, or are $C_3-C_8$-cycloalkyl, $C_3-C_8$-cycloalkenyl, heterocyclyl having 3 to 7 ring atoms, aryl, heteroaryl or arylcarbonyl, where each of the 6 last-mentioned radicals is unsubstituted or substituted by one or more radicals from the group consisting of $C_1$–$C_8$-alkyl, halogen, $C_1$–$C_8$-haloalkoxy, nitro, cyano, hydroxyl, $C_1$–$C_8$-alkoxy and $C_1$–$C_8$-alkoxy, in which one or more, preferably up to three, $CH_2$ groups which are not bonded directly to one another are replaced by oxygen, and $C_1$–$C_8$-alkylthio, $C_1$–$C_6$-alkylsulfonyl, $C_2$–$C_8$-alkenylthio, $C_2$–$C_8$-alkynylthio, $C_2$–$C_8$-alkenyloxy, $C_2$–$C_8$-alkynyloxy, $C_3$–$C_7$-cycloalkyl, $C_3$–$C_7$-cycloalkoxy, and amino, mono- and di-($C_1$–$C_4$-alkyl) amino, or $R^4$ and $R^5$ together are a $C_2$–$C_4$-alkylene chain or a $C_2$–$C_4$-alkenylene chain which is unsubstituted or substituted by 1 or 2 radicals from the group consisting of methyl, ethyl, methoxy, ethoxy and halogen, $R^6$ is hydrogen, $C_1$–$C_4$-alkyl, $C_2$–$C_4$-alkenyl, $C_2$–$C_4$-alkynyl, $C_6$–$C_{12}$-aryl, heteroaryl, benzyl, $C_1$–$C_4$-alkoxy, acyloxy, such as ($C_1$–$C_4$-alkyl)carbonyloxy, or unsubstituted or substituted phenylcarbonyloxy, or hydroxyl, —NH—CO—$NH_2$, —NH—CS—$NH_2$, mono- and di-($C_1$–$C_4$-alkyl)amino, —NH-acyl, —$NHSO_2$-($C_1$–$C_4$-alkyl), $C_6$–$C_{12}$-aryloxy, heteroaryloxy, NH—$SO_2$-aryl, or NH-aryl in which aryl or heteroaryl in the 4 last-mentioned radicals is unsubstituted or substituted by one or more radicals from the group consisting of halogen, nitro, ($C_1$–$C_4$)-alkyl, ($C_1$–$C_4$)-alkoxy, ($C_1$–$C_4$)-haloalkyl and ($C_1$–$C_4$)-haloalkoxy, T is O, S, $NR^7$, $NOR^7$ or NO-acyl, Q is O or S, q is a integer from 0 to 4, i is a serial number which, if q is not equal to 0, adopts all integers from 1 to q, where q is as defined above, $X_i$ independently of one another, are O, S, $NR^7$ or N—($A_i$—$X_i$—)q—R, $A_i$ independently of one another, are unsubstituted or substituted $C_1$–$C_6$-alkylene, $C_2$–$C_6$-alkenylene, $C_2$–$C_6$-alkynylene, $C_3$–$C_6$-cycloalkylene, $C_3$–$C_6$-cycloalkenylene, heterocyclylene, arylene or heteroarylene, and $R^7$ independently of one another, are H, $C_1$–$C_4$-alkyl, $C_2$–C4-alkenyl, $C_2$–$C_1$-alkynyl, $C_3$–$C_6$-cycloalkyl, $C_3$–$C_6$-cycloalkenyl, heterocyclyl, aryl or heteroaryl.

In the formula (I) and below, the alkyl, alkoxy, haloalkyl, haloalkoxy, alkylamino and alkylthio radicals and the corresponding unsaturated and/or substituted radicals in the carbon skeleton are each straight-chain or branched. Unless specifically stated, these radicals in which the carbon skeletons have 1 to 4 carbon atoms or in the case of unsaturated groups have 2 to 4 carbon atoms are preferred. Alkyl radicals, also in combination meanings such as alkoxy, haloalkyl, etc., are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals have the meaning of the possible unsaturated radicals corresponding to the alkyl radicals, alkenyl is, for example, allyl, 1-methylprop-2-en-1-yl, 2-methylprop-2-en-1-yl, but-2-en-1-yl, but-3-en-1-yl, 1-methyl-but-3-en-1-yl and 1-methyl-but-2-en-1-yl; alkynyl is, for example, propargyl, but-2-yn-1-yl, but-3-yn-1-yl, 1-methyl-but-3-yn-1-yl. Halogen is fluorine, chlorine, bromine or iodine, preferably fluorine, chlorine or bromine, in particular fluorine or chlorine. Haloalkyl, -alkenyl and -alkynyl are partially or fully halogen-substituted alkyl, alkenyl and alkynyl respectively, for example, $CF_3$, $CHF_2$, $CH_2F$, $CF_3CF_2$, $CH_2FCHCl$, $CCl_3$, $CHCl_2$ or $CH_2CH_2Cl$; haloalkoxy is, for example, $OCF_3$, $OCHF_2$, $OCH_2F$, $CF_3CF_2O$ or $OCH_2CF_3$. The corresponding applies to haloalkenyl and other halogen-substituted radicals.

Aryl is, for example, phenyl, naphthyl, tetrahydronaphthyl, indenyl, indanyl, pentalenyl, flubrenyl and the like, preferably phenyl; aryloxy is preferably the oxy radicals corresponding to said aryl radicals, in particular phenoxy.

Heteroaryl and heteroaryl in heteroaryloxy are, for example, pyridyl, pyrimidinyl, pyridazinyl, pyrazinyl, thienyl, thiazolyl, oxazolyl, furyl, pyrrolyl, pyrazolyl and imidazolyl, but also bicyclic or polycyclic aromatic or araliphatic compounds, for example quinolinyl, benzoxazolyl, etc.

Substituted aryl or aryloxy, heteroaryl, heteroaryloxy, phenyl, phenoxy, benzyl, benzyloxy and substituted bicyclic radicals containing aromatic moieties are, for example, a substituted radical derived from the unsubstituted parent structure, where the substituents are, for example, one or more, preferably 1, 2 or 3, radicals from the group consisting of halogen, alkyl, haloalkyl, alkoxy, haloalkoxy, hydroxyl, amino, nitro, cyano, alkoxycarbonyl, alkylcarbonyl, formyl, carbamoyl, mono- and dialkylaminocarbonyl, mono- and dialkylamino, alkylsulfinyl and alkylsulfonyl, and in the case of radicals containing carbon atoms those having 1 to 4 carbon atoms, in particular 1 or 2 carbon atoms, are preferred.

Preference is generally given to substituents from the halogen group, for example fluorine and chlorine, $C_1$–$C_4$-alkyl, preferably methyl or ethyl, $C_1$–$C_4$-haloalkyl, preferably trifluoromethyl, $C_1$–$C_4$-alkoxy, preferably methoxy or ethoxy, $C_1$–$C_4$-haloalkoxy, nitro and cyano. Particular preference is given to the substituents methyl, methoxy and chlorine.

Substituted or unsubstituted phenyl is, for example, phenyl which is unsubstituted or monosubstituted or polysubstituted, preferably up to trisubstituted, by identical or different radicals from the group consisting of halogen, ($C_1$–$C_4$)-alkyl, ($C_1$–$C_1$)-alkoxy, ($C_1$–$C_1$)-haloalkyl, ($C_1$–$C_1$)-haloalkoxy and nitro, for example o-, m- and p-tolyl, dimethylphenyl, 2-, 3- and 4-chlorophenyl, 2-, 3- and 4-trifluoro- and -trichlorophenyl, 2,4-, 3,5-, 2,5- and 2,3-dichlorophenyl, and o-, m- and p-methoxyphenyl.

A three- to seven-membered heterocyclic radical as described above is preferably derived from benzene, in which at least one CH has been replaced by N and/or at least two adjacent CH pairs have been replaced by NH, S and/or O. The radical may be benzo-fused. If desired, it can be partially or fully hydrogenated, and is then also known as heterocyclyl. Particularly suitable radicals are those such as oxiranyl, pyrrolidyl, piperidyl, dioxolanyl, pyrazolyl, morpholyl, furyl, tetrahydrofuryl, indolyl, quinolinyl, pyrimidyl, azepinyl, triazolyl, thienyl and oxazolyl.

Acyl is, for example, formyl, alkylcarbonyl, such as ($C_1$–$C_4$-alkyl)carbonyl, phenylcarbonyl, in which the phenyl ring may be substituted, for example as shown above for phenyl, or alkoxycarbonyl, phenoxycarbonyl, benzyloxycarbonyl, alkylsulfonyl and other radicals of organic acids.

Some compounds of the formula I contain one or more asymmetric carbon atoms or double bonds, which are not indicated separately in the formula I. The possible stereoisomers defined by their specific spatial shape, such as enantiomers, diastereomers, E- and Z-isomers, and mixtures thereof, are, however, all covered by the formula I.

The compounds of the formula I which are derived from carboxylic acids can form salts in which the radical R is replaced by an equivalent of a cation which is suitable for agriculture. These salts are, for example, metal salts, in particular alkali metal or alkaline earth metal salts, but also ammonium salts or salts with organic amines, and salts which contain sulfonium or phosphonium ions as cations.

Suitable salt formers are, in particular, metals and organic nitrogen bases, especially quaternary ammonium bases. Metals which are suitable here for salt formation are alkaline earth metals, such as magnesium or calcium, but especially alkali metals, such as lithium and in particular potassium and sodium.

Examples of nitrogen bases which are suitable for salt formation are primary, secondary or tertiary aliphatic and aromatic amines, which may be hydroxylated on the hydrocarbon radical, such as methylamine, ethylamine, propylamine, isopropylamine, the four isomeric butylamines, dimethylamine, diethylamine, dipropylamine, diisopropylamine, di-N-butylamine, pyrrolidine, piperidine, morpholine, trimethylamine, triethylamine, tripropylamine, quinuclidine, pyridine, quinoline, isoquinoline and methanolamine, ethanolamine, propanolamine, dimethanolamine, diethanolamine or triethanolamine.

Examples of quaternary ammonium bases are tetraalkylammonium cations in which the alkyl radicals, independently of one another, are straight-chain or branched $C_1$–$C_6$-alkyl groups, such as the tetramethylammonium cation, the tetraethylammonium cation or the trimethylethylainmonium cation, and furthermore the trimethylbenzylammonium cation, the triethylbenzylammonium cation and the trimethyl-2-hydroxyethylammonium cation.

Particularly preferred salt formers are the ammonium cation and di- and trialkylammonium cations in which the alkyl radicals, independently of one another, are straight-chain or branched, unsubstituted or hydroxyl-substituted ($C_1$–$C_6$)-alkyl groups, such as, for example, the dimethylammonium cation, the trimethylammonium cation, the triethylammonium cation, the di-(2-hydroxyethyl)ammonium cation and the tri-(2-hydroxyethyl)ammonium cation.

Of particular interest are compounds of the formula (I), or salts thereof, in which
$R^3$ is hydrogen, $C_1$–$C_4$-alkyl, $C_1$–$C_4$-alkoxy, $C_5$–$C_6$-cycloalkyl, trimethylsilyl, triethylsilyl or a radical of the formula Ar'X'—, in which Ar' and X40 are defined analogously to Ar and X respectively,
X is O, S, NH, $NCH_3$ or $NC_2H_5$,
Ar is a radical of the formula

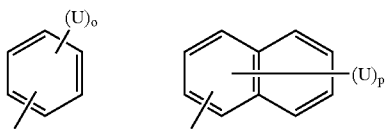

in which
(U) are identical or different radicals which, independently of one another, are hydrogen, halogen, such as fluorine, chlorine, bromine and iodine, cyano, nitro, amino or $C_1$–$C_4$-haloalkyl, $C_1$–$C_4$-haloalkoxy, $C_1$–$C_4$-alkyl, $C_1$–$C_4$-alkoxy, mono-($C_1$–$C_4$-alkyl) amino, di-($C_1$–$C_4$-alkyl) amino, $C_1$–$C_4$-alkylthio or $C_1$–$C_4$-alkylsulfonyl, and
o is an integer from 1 to 3, and
p is an integer from 1 to 3, or
Ar is a monocyclic or bicyclic heteroaryl radical from the group consisting of furyl, thienyl, pyrrolyl, pyrazolyl, thiazolyl, oxazolyl, pyridinyl, pyrimidinyl, pyrazinyl, pyridazinyl and quinolinyl, which is unsubstituted or substituted by one to three of the abovementioned radicals U.

Of particular interest are also compounds of said formula (I) and salts thereof in which
R is hydrogen, $C_1$–$C_8$-alkyl, $C_4$–$C_7$-cycloalkyl, $C_2$–$C_8$-alkenyl, $C_2$–$C_8$-alkynyl, heterocyclyl, phenyl or heteroaryl,
where each of the 7 last-mentioned radicals, independently of one another, is unsubstituted or substituted by one or more radicals from the group consisting of halogen, cyano, thio, nitro, hydroxyl, $C_1$–$C_4$-alkyl, the latter only in the case of cyclic radicals, $C_1$–$C_4$-haloalkyl, $C_1$–$C_4$-alkoxy, $C_2$–$C_4$-alkenyloxy, $C_2$–$C_4$-alkynyloxy, $C_1$–$C_4$-haloalkoxy, $C_1$–$C_4$-alkylthio, $C_2$–$C_4$-alkenylthio, $C_2$–$C_4$-alkynylthio, $C_5$–$C_6$-cycloalkyl, $C_5$–$C_6$-cycloalkoxy, amino, mono- and di-($C_1$–$C_4$-alkyl) amino, ($C_1$–$C_6$-alkoxy)carbonyl, radicals of the formulae —$SiR'_3$, —O—$NR'_2$, —O—N=$CR'_2$, —N=$CR'_2$, in which the R' in said formulae are, independently of one another, hydrogen, $C_1$—$C_2$-alkyl or phenyl or in pairs are a $C_2$–$C_5$-alkylene chain, or
compounds in which
$R^T$ is a radical of the formula —CO—R, —$NR^fR^g$ or —N=$CR^hR^i$, where R, $R^f$, $R^g$, $R^h$ and $R^i$ are as defined above.

R is preferably hydrogen, $C_1$–$C_8$-alkyl, $C_5$—$C_6$-cycloalkyl, $C_2$–$C_8$-alkenyl or $C_2$–$C_8$-alkynyl, where each of the 4 last-mentioned radicals, independently of one another, are unsubstituted or substituted by one or more radicals from the group consisting of halogen, cyano, nitro, $C_1$–$C_4$-alkoxy, $C_2$–$C_4$-alkenyloxy, $C_2$–$C_4$-alkynyloxy, $C_5$—$C_6$-cycloalkyl, $C_5$–C6cycloalkoxy, mono- and di-($C_1$–$C_4$-alkyl)amino, radicals of the formulae —$SiR'_3$, —O—N=$CR'_2$, —N=$CR'_2$, in which the R' in said formulae are, independently of one another, hydrogen, $C_1$–$C_2$-alkyl or phenyl or in pairs are a $C_2$–$C_5$-alkylene chain.

$R^T$ is preferably —CO—R, where R is as defined above, or —$NR^fR^g$ or —N=$CR^hR^i$, in which
$R^f$ and $R^g$, independently of one another, are H, $C_1$–$C_2$-alkyl, benzyl or phenyl or together with the nitrogen atom are pyrrolidin-1-yl, piperidin-1-yl, morpholin-4-yl, piperazin-1-yl or imidazol-1-yl, and
$R^h$ and $R^i$, independently of one another, are H, $C_1$–$C_2$-alkyl, benzyl or phenyl.

Of particular interest are also compounds of said formula (I) and salts thereof, in which
$R^4$ and $R^5$ are identical or different and, independently of one another, are hydrogen, $C_1$–$C_4$-alkyl, $C_2$–$C_4$-alkenyl, $C_2$–$C_4$-alkynyl, $C_5$–$C_6$-cycloalkyl or $C_5$–$C_6$-cycloalkenyl,
and compounds in which
$R^6$ is hydrogen, $C_1$–$C_4$-alkyl, phenyl, benzyl, hydroxyl, NH—CO—$NH_2$, —NH-aryl or $C_1$–$C_4$-alkoxy.

Of particular interest are also compounds of the said formula (I) and salts thereof, in which
T is O, S or $NR^7$, preferably O or $NR^7$,
Q is O or S, preferably O,
q is an integer from 0 to 4,
i is a serial number which, if q is not equal to O, adopts all integers from 1 to q, where q is as defined above,
$X_i$ independently of one another, are O, S, $NR^7$ or N—($A_i$—$X_i$—$)_q$—R, $A_i$ independently of one another, are unsubstituted, or substituted $C_1$–$C_4$-alkylene, $C_2$–$C_4$-alkenylene or $C_5$–$C_6$-cycloalkylene, preferably $C_1$–$C_4$-alkylene, $R^7$ independently of one another, are H, $C_1$—$C_4$-alkyl, $C_2$–$C_4$-alkenyl, $C_2$–$C_4$-alkynyl or $C_5$–$C_6$-cycloalkyl.

Preference is given to compounds of the formula (I), and salts thereof, in which $R^1$ and $R^2$, independently of one another, are radicals of the formula

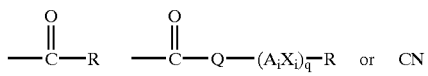

in which R, T, Q, $A_i$, $X_i$ and q are as defined above.

The invention also relates to a process for protecting crop plants, preferably cereal, rice or corn plants, against phytotoxic side-effects of herbicides, which comprises applying an effective amount of at least one compound of the formula I, or a salt thereof, to the plants, plant seeds or cultivated area before, after or simultaneously with the abovementioned herbicidal active compound.

The invention furthermore relates to the use of compounds of the formula I, or salts thereof, for protecting crop plants against phytotoxic side-effects of herbicides.

Some of the compounds of the formula I are known, such as, for example, diethyl 2-(quinoline-8-yl-mercapto) malonate and ethyl 2-(quinoline-8-mercapto)acetoacetate (G. Buchmann, J. prakt. Chem. 1965, 141); diethyl 4-chlorophenoxymalonate (J. Izv. Sibirsk. Ord. Akad. Nauk. SSSR 1962 (11), 145–8, see Chem. Abstracts 59:5051 g (1963)). However, their safener action had hitherto not been disclosed.

The invention also relates to all compounds of the formula I which had not been disclosed hitherto.

The compounds of the formula I can be prepared by processes which are known in general terms; see, for example, EP-A-4433; J. Am. Chem. Soc. 62 (1990) 1154; J. Org. Chem. 36 (1971) 3646; Chem. Abstr. 111 (1988) 133625 q; EP-A-326328; J. Am. Chem. Soc. 94 (1972) 712; Ukr. Khim. Zh. (Russ. Ed.) 56 (1990) 638; Chem. Abstr. 114 (1991) 42155 g; Chem. Pharm. Bull. 17 (1969) 419; Chem. Lett. 1973, 287; J. Chem. Soc. Chem. Comm. 1979, 50; Bull. Chem. Soc. Jpn. 45 (1972) 866; J. Org. Chem. 39 (1974) 1233 and the references cited therein.

Thus, the. compounds of the formula I according to the invention can be prepared by a) reacting a compound of the formula Ar—X—H, in which Ar and X are as defined under formula I, with a compound of the formula II

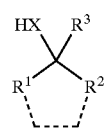

(II)

in which

L is a leaving group, such as, for example, chlorine, bromine, methanesulfonyl or toluenesulfonyl, and $R^1$, $R^2$ and $R^3$ are as defined under said formula I, or b) reacting a compound of the formula Ar—W with a compound of the formula III

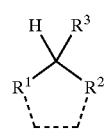

(III)

where w is a leaving group, such as, for example, chlorine, bromine, methanesulfonyl or toluenesulfonyl, and Ar, X, $R^1$, $R^2$ and $R^3$ are as defined under said formula I, or c) reacting a compound of the formula AR—X—W with a compound of the formula IV

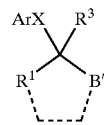

(IV)

where

W is a leaving group, such as, for example, chlorine, methanesulfonyl, toluenesulfonyl, dialkylamino, diacylamino or arylthio, and Ar, X, $R^1$, $R^2$ and $R^3$ are as defined under formula I, or d) transesterifying an aryl- or heteroaryloxycarboxylic acid derivative of the formula V

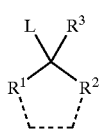

(V)

in which

Ar, X, $R^1$ and $R^3$ are as defined under formula I, and B' is a group of the formula

are bonded to one another and together are a group of the formula —CO—$Q^1$—D—$Q^2$—CO—, where T, Q, $A_i$, $X_i$, q, R, $R^T$ $Q^1$, $Q^2$ and D are defined analogously to the radicals of the same names in formula I, with alcohols or mercaptans.

The reactions in variant a) are preferably carried out in dipolar aprotic solvents, such as dimethyl sulfoxide, N,N-dimethylformamide, methyl isobutyl ketone, dioxane or acetone, at elevated temperature, in particular at between 40 and 180° C. in the presence of a base, in particular alkali metal carbonates, such as, for example, potassium carbonate.

The reactions in variant b) are preferably carried out in aprotic solvents, such as toluene, N,N-dimethylformamide, acetonitrile, methyl isobutyl ketone, dioxane or acetone, at elevated temperature, in particular at between 40 and 180° C. in the presence of a base, in particular alkali metal carbonates, such as, for example, potassium carbonate.

The reactions in variant c) are preferably carried out in aprotic solvents, such as dimethyl sulfoxide, N,N-dimethylformamide, tetrahydrofuran, dioxane or methylene chloride, or in alcohols, such as methanol, ethanol, at from room temperature to elevated temperature, in particular at between 20 and 100° C. in the presence of a base, in particular alkali metal alkoxides, such as, for example, sodium methoxide or sodium ethoxide.

The transesterifications or amidations in variant d) are principally carried out by reacting a compound of the formula V with the alcohols or the amines at elevated temperatures, in particular at the reflux temperature of the reaction mixture, in the presence of titanium alkoxides as catalyst.

Compounds of the formula I reduce or suppress phytotoxic side-effects of herbicides which can occur when the herbicides are used in crops of useful plants, and can therefore be referred to in the usual manner as antidotes or safeners.

The compounds of the formula I according to the invention can be applied together with herbicidal active compounds or in any desired sequence and are then capable of reducing or fully eliminating harmful side-effects of these herbicides in crop plants without impairing the effectiveness of these herbicides against weeds.

This allows the area of application of conventional crop-protection agents to be very substantially broadened. Herbicides whose phytotoxic side-effects on crop plants can be reduced by means of compounds of the formula I are, for example, carbamates, thiocarbamates, haloacet anilides, substituted phenoxy-, naphthoxy- and phenoxy-phenoxycarboxylic acid derivatives and heteroaryloxy-phenoxyalkanecarboxylic acid derivatives, such as quinolyloxy-, quinoxalyloxy-, pyridyloxy-, benzoxalyloxy- and benzothiazolyloxyphenoxyalkanecarboxylic esters, cyclohexanedione derivatives, imidazolinones, pyrimidyl-oxypyridinecarboxylic acid derivatives, pyrimidyloxyben-zoic acid derivatives, sulfonylureas, triazolopyrimidine-sulfonamide derivatives and S-(N-aryl-N-alkylcarbamoylmethyl)dithiophosphonic esters. Preference is given to phenoxyphenoxy- and heteroaryloxy-phenoxycarboxylic esters and salts, sulfonylureas and imidazolinones.

Suitable herbicides which can be combined with the safeners according to the invention are, for example:

A) Herbicides of the ($C_1$–$C_4$)-alkyl, ($C_2$–$C_4$)alkenyl and ($C_3$–$C_4$)alkynyl phenoxyphenoxy- and heteroaryloxyphenoxy-carboxylate, such as A1) Phenoxyphenoxy- and benzyloxyphenoxycarboxylic acid derivatives, for example
methyl 2-(4-(2,4-dichlorophenoxy)phenoxy)propionate (diclofop-methyl),
methyl 2-(4-(4-bromo-2-chlorophenoxy)phenoxy) propionate (see DE-A-2601548),
methyl 2-(4-(4-bromo-2-fluorophenoxy)phenoxy) propionate (see U.S. Pat. No. 4,808,750),
methyl 2-(4-(2-chloro-4-trifluoromethylphenoxy)phenoxy) propionate (see DE-A-2433067),
methyl 2-(4-(2-fluoro-4-trifluoromethylphenoxy)phenoxy) propionate (see U.S. Pat. No. 4,808,750),
methyl 2-(4-(2,4-dichlorobenzyl)phenoxy)propionate (see DE-A-2417487),
ethyl 4-(4-(4-trifluoromethylphenoxy)phenoxy)pent-2-enoate,
methyl 2-(4-(4-trifluoromethylphenoxy)phenoxy) propionate (see DE-A-2433067), A2) "Monocyclic" heteroaryloxyphenoxyalkanecarboxylic acid derivatives, for example,
ethyl 2-(4-(3,5-dichloropyridyl-2-oxy)phenoxy)propionate (see EP-A-2925),
propargyl 2-(4-(3,5-dichloropyridyl-2-oxy)phenoxy) propionate (see EP-A-3114),
methyl 2-(4-(3-chloro-5-trifluoromethyl-2-pyridyloxy) phenoxypropionate (see EP-A-3890),
ethyl 2-(4-(3-chloro-5-trifluoromethyl-2-pyridyloxy) phenoxy)propionate (see EP-A-3890),
propargyl 2-(4-(5-chloro-3-fluoro-2-pyridyloxy)phenoxy) propionate (EP-A-191736),
butyl 2-(4-(5-trifluoromethyl-2-pyridyloxy)phenoxy) propionate (fluazifop-butyl), A3) "Bicyclic" heteroaryloxyphenoxyalkanecarboxylic acid derivatives, for example
methyl and ethyl 2-(4-(6-chloro-2-quinoxalyloxy)phenoxy) propionate (quizalofop-methyl and -ethyl),
methyl 2-(4-($^6$-fluoro-2-quinoxalyloxy)phenoxy)propionate (see J. Pest. Sci. Vol. 10, 61 (1985)),
2-(4-(6-chloro-2-quinoxalyloxy)phenoxy)propionic acid and the 2-isopropylideneaminooxyethyl ester thereof. (propaquizafop and ester),
ethyl 2-(4-(6-chlorobenzoxazol-2-yl-oxy)phenoxy) propionate (Fenoxaprop-ethyl), and the D(+) isomer thereof (Fenoxaprop-P-ethyl),
ethyl 2-(4-(6-chlorobenzothiazol-2-yloxy) phenoxypropionate (see DE-A-2640730),
tetrahydrofur-2-yl-methyl 2-(4-(6-chloroquinoxalyloxy) phenoxypropionate (see EP-A-323 727), B) Herbicides from the sulfonylurea series, such as, for example, pyrimidine- or triazinylaminocarbonyl-[benzene, pyridine, pyrazole, thiophene, and (alkylsulfony)alkylamino]sulfamides. Preferred substituents on the pyrimidine ring or triazine ring are alkoxy, alkyl, haloalkoxy, haloalkyl, halogen or dimethylamino, where all the substituents can be combined, independently of one another. Preferred substituents in the benzene, pyridine, pyrazole, thiophene or (alkylsulfonyl) alkylamino moiety are alkyl, alkoxy, halogen, nitro, alkoxycarbonyl, aminocarbonyl, alkylaminocarbonyl, dialkylaminocarbonyl, alkoxyaminocarbonyl, alkyl, alkoxyaminocarbonyl, haloalkoxy, haloalkyl, alkylcarbonyl, alkoxyalkyl, and (alkanesulfonyl) alkylamino. Suitable sulfonylureas are, for example, B1) Phenyl- and benzylsulfonylureas and related compounds, for example,
1-(2-chlorophenylsulfonyl)-3-(4-methoxy-6-methyl-1,3,5-triazin-2-yl)urea (chlorsulfuron),
1-(2-ethoxycarbonylphenylsulfonyl)-3-(4-chloro-6-methoxypyrimidine-2-yl)urea (chlorimuron-ethyl),
1-(2-methoxyphenylsulfonyl)-3-(4-methoxy-6-methyl-1,3,5-triazin-2-yl)urea (metsulfuron-methyl),
1-(2-chloroethoxyphenylsulfonyl)-3-(4-methoxy-6-methyl-1,3,5-triazin-2-yl)urea (triasulfuron),
1-(2-methoxycarbonylphenylsulfonyl)-3-(4,6-dimethylpyrimidin-2-yl)urea (sulfometuron-methyl),
1-(2-methoxycarbonylphenylsulfonyl)-3-(4-methoxy-6-methyl-1,3,5-triazin-2-yl)-3-methylurea (tribenuron methyl),
1-(2-methbxycarbonylbenzylsulfonyl)-3-(4,6-dimethoxypyrimidin-2-yl)urea (bensulfuron-methyl),
1-(2-methoxycarbonylphenylsulfonyl)-3-(4,6-bis (difluoromethoxy)pyrimidin-2-yl)urea (primisulfuron-methyl),
3-(4-ethyl-6-methoxy-1,3,5-triazin-2-yl)-1-(2,3-dihydro-1, 1-dioxo-2-methylbenzo[b]thiophenee-7-sulfonyl)urea (see EP-A-79683),
3-(4-ethoxy-6-ethyl-1,3,5-triazin-2-yl)-1-(2,3-dihydro-1,1-dioxo-2-methylbenzo[b]thiophene-7-sulfonyl)urea (see EP-A-79683), B2) Thienylsulfonylureas, for example 1-(2-methoxycarbonylthiophen-3-yl)-3-(4-methoxy-6-methyl-1,3,5-triazin-2-yl)urea (thifensulfuron-methyl), B3) Pyrazolylsulfonylureas, for example 1-(4-ethoxycarbonyl-1-methylpyrazol-5-ylsulfonyl)-3-(4,6-dimethoxypyrimidin-2-yl)urea (pyrazosulfuron-methyl), methyl 3-chloro-5-(4,6-dimethoxypyrimidin-2-ylcarbamoylsulfamoyl)-1-methylpyrazole-4-carboxylate (see EP 282613), methyl 5-(4,6-dimethylpyrimidin-2-ylcarbamoylsulfamoyl)-1-(2-pyridyl)pyrazole-4-carboxylate (NC-330, see Brighton Crop Prot. Conference—Weeds—1991, Vol. 1, 45 ff.), B4) Sulfonediamide derivatives, for example, 3-(4,6-dimethoxypyrimidin-2-yl)-1-(N-methyl-N-methylsulfonylaminosulfonyl)urea (amidosulfuron) and structural analogs (see EP-A-0131258 and Z. Pfl. Krankh. Pfl. Schutz 1990, Special Issue XII, 489–497), B5) Pyridylsulfonylurea, for example 1-(3-N,N-dimethylaminocarbonylpyridin-2-ylsulfonyl)-3-(4,6-dimethoxypyrimidin-2-yl)urea (nicosulfuron), 1-(3-ethylsulfonylpyridin-2-ylsulfonyl)-3-(4,6-dimethoxypyrimidin-2-yl)urea (DPX-E 9636, see Brighton Crop Prot. Conf.—Weeds—1989, pp. 23 ff.), Pyridylsulfonylureas, as described in DE-A-4000503 and DE-A-4030577, preferably those of the formula

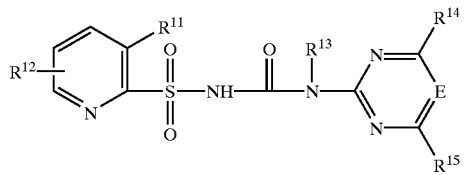

in which

E is CH or N, preferably CH, $R^{11}$ is iodine or $NR^{16}R^{17}$, $R^{12}$ is H, halogen, cyano, $C_1$–$C_3$-alkyl, $C_1$–$C_3$-alkoxy, $C_1$–$C_3$-haloalkyl, $C_1$–$C_3$-haloalkoxy, $C_1$–$C_3$-alkylthio, ($C_1$–$C_3$-alkoxy)-$C_1$–$C_3$-alkyl, ($C_1$–$C_3$-alkoxy) carbonyl, mono- or di($C_1$–$C_3$-alkyl)amino, $C_1$–$C_3$-alkylsulfinyl or -sulfonyl, $SO_2$—$NR^aR^b$ or $CO$—$NR^aR^b$, in particular H, $R^a$ and $R^b$, independent of one another, are H, $C_1$–$C_3$-alkyl, $C_1$–$C_3$-alkenyl, $C_1$–$C_3$-alkynyl, or together are —$(CH_2)_4$—, —$(CH_2)_5$— or —$(CH_2)_2$—O—$(CH_2)_2$—, $R^{13}$ is H or $CH_3$, $R^{14}$ is halogen, $C_1$–$C_2$-alkyl, $C_1$–$C_2$-alkoxy, $C_1$–$C_2$-haloalkyl, preferably $CF_3$, or $C_1$–$C_2$-haloalkoxy, preferably $OCHF_2$ or $OCH_2CF_3$, $R^{15}$ is $C_1$–$C_2$-alkyl, $C_1$–$C_2$-haloalkoxy, preferably $OCHF_2$, or $C_1$–$C_2$-alkoxy, and $R^{16}$; is $C_1$–$C_4$-alkyl, and $R^{17}$ is $C_1$–$C_4$-alkylsulfonyl or $R^{16}$ and $R^{17}$ together are a chain of the formula —$(CH_2)_3SO_2$— or —$(CH_2)_4SO_2$—, for example, 3=(4,6-dimethoxypyrimidin-2-yl)1-(3-N-methylsulfonyl-N-methylaminopyridin-2-yl) sulfonylurea, or salts thereof, B6) Alkoxyphenoxysulfonylureas, as described in EP-A-0342569, preferably those of the formula

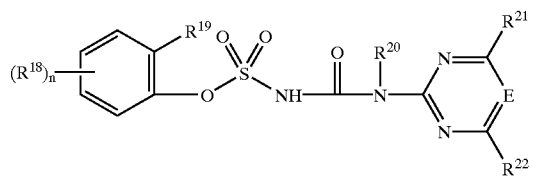

in which

E is CH or N, preferably CH, $R^{18}$ is ethoxy, propoxy or isopropoxy, $R^{19}$ is hydrogen, halogen, $NO_2$, $CF_3CN$, $C_1$–$C_4$-alkyl, $C_1$–$C_4$-alkoxy, $C_1$–$C$,-alkylthio or ($C_1$–$C_3$-alkoxy)-carbonyl, preferably in the 6-position on the phenyl ring, n is 1, 2 or 3, preferably 1, $R^{20}$ is hydrogen, $C_1$–$C_4$-alkyl or $C_3$–$C_4$-alkenyl, $R^{21}$ and $R^{22}$, independently of one another, are halogen, $C_1$–$C_2$-alkyl, $C_1$–$C_2$-alkoxy, $C_1$–$C_2$-haloalkyl, $C_1$–$C_2$-haloalkoxy or ($C_1$–$C_2$-alkoxy)-$C_1$–$C_2$-alkyl, preferably $OCH_3$ or $CH_3$, for example 3-(4,6-dimethoxypyrimidin-2-yl)-1-(2-ethoxyphenoxy)sulfonylurea, or salts thereof, and other related sulfonylurea derivatives, and mixtures thereof, C) Chloroacetanilide herbicides, such as N-methoxymethyl-2,6-diethylchloroacetanilide (alachlor), N-(3'-methoxyprop-2'-yl)-2-methyl-6-ethylchloroacetanilide (metolachlor), 2',6'-dimethyl-N-(3-methyl-1,2,4-oxadiazol-5-ylmethyl) chloroacetanilide N-(2,6-dimethylphenyl)-N-(1-pyrazolylmethyl) chloroacetamide (metazachlor), D) Thiocarbamates, such as S-ethyl N,N-dipropylthiocarbamate (EPTC) or S-ethyl N,N-diisobutylthiocarbamate (butylate), E) Cyclohexanedione derivatives, such as methyl 3-(1-allyloxyiminobutyl)-4-hydroxy-6,6-dimethyl-2-oxocyclohex-3-enecarboxylate (alloxydim), 2-(1-ethoxyiminobutyl)-5-(2-ethylthiopropyl)-3-hydroxycyclohex-2-en-1-one (sethoxydim), 2-(1-ethoxyiminobutyl)-5-(2-phenylthiopropyl)-3-hydroxycyclohex-2-en-1-one (cloproxydim), 2-(1-(3-chloroallyloxy)iminobutyl)-5-[2-(ethylthio)propyl]-3-hydroxycyclohex-2-en-1-one, 2-(1-(3-chloroallyloxy)iminopropyl)-5-[2-(ethylthio)propyl]-3-hydroxycyclohex-2-en-1-one (clethodim), 2-(1-(ethoxyimino)butyl)-3-hydroxy-5-(thian-3-yl) cyclohex-2-enone (cycloxydim) or 2-(1-ethoxyiminopropyl)-5-(2,4,6-trimethylphenyl)-3-hydroxycyclohex-2-en-1-one (tralkoxydim), F)2-(4-alkyl-5-oxo-2-imidazolin-2-yl)benzoic acid derivatives or 2-(4-alkyl-5-oxo-2-imidazolin-2-yl) heteroarylcarboxylic acid derivatives, such as, for example, methyl 2-(4-isopropyl-4-methyl-5-oxo-2-imidazolin-2-yl)-5-methylbenzoate and 2-(4-isopropyl-4-methyl-5-oxo-2-imidazolin-2-yl)-4-methylbenzoic acid (imazamethabenz), 5-ethyl-2-(4-isopropyl-4-methyl-5-oxo-2-imidazolin-2-yl) pyridine-3-carboxylic acid (imazathapyr), 2-(4-isopropyl-4-methyl-5-oxo-2-imidazolin-2-yl) quinoline-3-carboxylic acid (imazaquin), 2-(4-isopropyl-4-methyl-5-oxo-2-imidazolin-2-yl)pyridine-3-carboxylic acid (imazapyr), 5-methyl-2-(4-isopropyl-4-methyl-5-oxo-2-imidazolin-2-yl)pyridine-3-carboxylic acid (imazethamethapyr), G) Triazolopyrimidinesulfonamide derivatives, for example N-(2,6-difluorophenyl)-7-methyl-1,2,4-triazolo-(1,5-c)-pyrimidine-2-sulfonamide (flumetsulam),
N-(2,6-dichloro-3-methylphenyl)-5,7-dimethoxy-1,2,4-triazolo-(1,5-c)-pyrimidine-2-sulfonamide,
N-(2,6-difluorophenyl)-7-fluoro-5-methoxy-1,2,4-triazolo-(1,5-c)-pyrimidine-2-sulfonamide,
N-(2,6-dichloro-3-methylphenyl)-7-chloro-5-methoxy-1,2,4-triazolo-(1,5-c)-pyrimidine-2-sulfonamide,
N-(2-chloro-6-methoxycarbonyl)-5,7-dimethyl-1,2,4-triazolo-(1,5-c)-pyrimidine-2-sulfonamide (see, for example, EP-A-343.752, and U.S. Pat. No. 4 988 812),
H) Benzoylcyclohexanedione derivatives, for example 2-(2-chloro-4-methylsulfonylbenzoyl)cyclohexane-1,3-dione (SC-0051, see EP-A-137963),
2-(2-nitrobenzoyl)-4,4-dimethylcyclohexane-1,3-dione (see EP-A-274634),
2-(2-nitro-3-methylsulfonylbenzoyl)-4,4,-dimethylcyclohexane-1,3-dione (see WO-91/13548),
J) Pyriinidinyloxypyrimidinecarboxylic acid derivatives and pyrimidinyloxybenzoic acid derivatives, for example benzyl 3-(4,6-dimethoxypyrimidin-2-yl)oxypyridine-2-carboxylate (EP-A-249 707),
methyl 3-(4,6-dimethoxypyrimidin-2-yl)oxypyridine-2-carboxylate (EP-A-249 707),
2,6-bis[(4,6-dimethoxypyrimidin-2-yl)oxy]benzoic acid (EP-A 321 846),
1-ethoxycarbonyloxyethyl 2,6-bis[(4,6-dimethoxypyrimidin-2-yl)oxy]benzoate (EP-A-472 113), and
K) S-(N-aryl-N-alkylcarbamoylmethyl)dithiophosphoric esters, such as
S-[N-(4-chlorophenyl)-N-isopropylcarbamoylmethyl] O,O-dimethyl dithiophosphate (anilofos).

The abovementioned herbicides from groups A to K are known to persons skilled in the art and are generally described in "The Pesticide Manual", British Crop Protection Council, 9th Edition, 1991, or 8th Edition, 1987, or in "Agricultural Chemicals Book II, Herbicides", by W. T. Thompson, Thompson Publications, Fresno Calif., USA, 1990, or in "Farm Chemicals Handbook '90", Meister Publishing Company, Willoughby, Oh, USA, 1990. Imazethamethapyr is disclosed in Weed Techn. 1991, Vol. 5, 430–438.

The herbicidal active compounds and the safeners mentioned can be applied together (as a ready-to-use formulation or in the tank-mix method) or in any desired sequence one after the other. The safener:herbicide weight ratio can vary within broad limits and is preferably in the range from 1:10 to 10:1, in particular from 1:10 to 5:1. The optimum amounts of both herbicide and safener depend on the type of herbicide used and on the safener used and on the type of plant crop to be treated and can be determined from case to case by appropriate preliminary experiments.

The main areas of application of the safeners are in particular cereal crops (wheat, rye, barley and oats), rice, corn, sorghum, but also cotton and soybeans, preferably cereals, rice and corn.

A particular advantage of the safeners of the formula I according to the invention is observed when they are combined with herbicides from the group consisting of the sulfonylureas and/or imidazolinones and with herbicides of the phenoxyphenoxy- and heteroaryloxyphenoxyalkanecarboxylic acid derivative type.

Some herbicides from these structural classes cannot be employed selectively or not sufficiently selectively, specifically in cereal crops and/or maize and rice. Combination with the safeners according to the invention allows excellent selectivities to be achieved in cereals, corn or rice, even for these herbicides.

The safeners of the formula I, depending on their properties, can be used for pretreatment of seed of the crop plant (seed dressing) or introduced into the seed drills before sowing or applied together with the herbicide before or after emergence of the plants. Preemergence treatment includes both treatment of the cultivated area before sowing and treatment of the sown cultivated areas, but before growth appears. Joint application with the herbicide is preferred. To this end, tank mixes and ready mixes can be employed.

The safener application rates required can vary within broad limits, depending on the indication and herbicide used and are generally in the range from 0.001 to 5 kg, preferably from 0.005 to 0.5 kg, of active compound per hectare.

The present invention therefore also relates to a process for protecting crop plants against phytotoxic side-effects of herbicides, which comprises applying effective amounts of a compound of the formula I to the plants, plant seeds or cultivated area before, after or simultaneously with the herbicide.

The invention also relates to crop-protection agents which contain an active compound of the formula I and conventional formulation auxiliaries, and to herbicides which contain an active compound of the formula I and a herbicide and, in the area of the crop protection, conventional formulation auxiliaries.

The compounds of the formula I and their combinations with one or more of said herbicides can be formulated in various ways, depending on which biological and/or chemical-physical parameters are pre-specified. Examples of suitable possible formulations are: wettable powders (WP), emulsifiable concentrates (EC), water-soluble powders (SP), water-soluble concentrates (SL), concentrated emulsions (EW), such as oil-in-water and water-in-oil emulsions, sprayable solutions or emulsions, capsule suspensions (CS), oil- or water-based dispersions (SC), suspoemulsions, suspension concentrates, dusts (DP), oil-miscible solutions (OL), dressings, granules (GR) in the form of microgranules, sprayable granules, coated granules and adsorption granules, granules for soil application or broadcasting, water-soluble granules (SG), also water-dispersible granules (WG), ULV formulations, microcapsules and waxes.

These individual formulation types are known in principle and are described, for example, in: Winnacker-Kuchler, "Chemische Technologie" [Chemical Technology], Volume 7, C. Hauser Verlag, Munich, 4th Edn., 1986; Wade van Valkenburg, "Pesticide Formulations", Marcel Dekker, N.Y., 1973; K. Martens, "Spray Drying Handbook", 3rd ed., 1979, G. Goodwin Ltd., London.

The formulation auxiliaries required, such as inert materials, surfactants, solvents and further additives, are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schödnfeldt, "Grenzflächenaktive Äthylenoxidaddukte", i[Surface-active Ethylene Oxide Adducts], Wiss. verlagsge sell., Stuttgart 1976; Winnacker-Küchler "Chemische Technologie", [Chemical Technology], Volume 7, C. Hauser Verlag Munich, 4th Edn., 1986.

Based on these formulations, combinations with other pesticidally active substances, fertilizers and/or growth regulators can also be prepared, for example in the form of a ready mix or a tank mix.

Wettable powders are uniformly water-dispersible preparations which, besides the active compound and in addition to a diluent or inert substance, also contain wetting agents, for example polyoxyethylated alkylphenols, polyoxyethylated fatty alcohols and fatty amines, fatty alcohol polyglycol ether sulfates, alkanesulfonates or alkylarylsulfonates, and dispersants, for example sodium ligninsulfonate, sodium 2,2-dinaphthylmethane-6-6'-disulfonate, sodium dibutylnaphthalenesulfonate or sodium oleoylmethyltaurate.

Emulsifiable concentrates are prepared by dissolving the active compound in an organic solvent, for example butanol, cyclohexanone, dimethylformamide, xylene or relatively high-boiling aromatic compounds or hydrocarbons, with addition of one or more emulsifiers. Examples of emulsifiers which can be used are: calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, (for example block polymers), alkylpolyethers, sorbitan fatty acid esters, polyoxyethylene-sorbitan fatty acid esters or polyoxyethylenesorbitol esters.

Dusts are obtained by grinding the active compound with finely divided solids, for example talc, natural clays, such as kaolin, bentonite and pyrophyllite, or diatomaceous earth.

Granules can be prepared either by spraying the active compound onto adsorptive, granulated inert material or by applying active compound concentrates to the surface of support materials, such as sand, kaolinites or granulated inert material, by means of adhesives, for example polyvinyl alcohol, sodium polyacrylate or mineral oils. Suitable active compounds can also be granulated in the usual way for the preparation of fertilizer granules—if desired as a mixture with fertilizers.

The agrochemical preparations generally contain from 0.1 to 99% by weight, in particular from 0.1 to 95% by weight, of active compounds of the formula I (antidote) and of the antidote/herbicide active compound mixture and from 1 to 99.9% by weight, in particular from 5 to 99.8% by weight, of a solid or liquid additive and from 0 to 25% by weight, in particular from 0.1 to 25% by weight, of a surfactant.

In wettable powders, the active compound concentration is, for example, from about 10 to 90% by weight, the remainder to 100% by weight comprising conventional formulation constituents. In the case of emulsifiable concentrates, the active compound concentration is from about 1 to 80% by weight of active compounds. Dust-form formulations contain from about 1 to 20% by weight of active compounds, sprayable solutions from about 0.2 to 20% by weight of active compounds. In the case of granules, such as water-dispersible granules, the active compound content depends partly on whether the active compound is in liquid or solid form. In general, the content in the case of water-dispersible granules is between 10 and 90% by weight.

In addition, said active compound formulations may contain the adhesives, wetting agents, dispersants, emulsifiers, penetrants, solvents, fillers or support materials which are conventional in each case.

For application, the formulations, in commercially available form, are, if appropriate, diluted in a conventional manner, for example by means of water in the case of wettable powders, emulsifiable concentrates, dispersions and water-dispersible granules. Dust-form preparations, granules and sprayable solutions are not usually further diluted with further inert substances before application. The "antidote" application rate necessary varies, inter alia, with the external conditions, such as temperature, humidity and the type of herbicide used.

The samples below serve to illustrate the invention:

A. Formulation Examples a) A dust is obtained by mixing 10 parts by weight of a compound of the formula I or of an active compound mixture comprising a herbicide and a compound of the formula I and 90 parts by weight of talc as inert material and comminuting the mixture in a hammer mill.

b) A readily water-dispersible wettable powder is obtained by mixing 25 parts by weight of a compound of the formula I or of an active compound mixture comprising a herbicide and a safener of the formula I, 64 parts by weight of kaolin-containing quartz as inert material, 10 parts by weight of potassium ligninsulfonate and 1 part by weight of sodium oleoylmethyltaurate as wetting agent and dispersant, and grinding the mixture in a pin mill.

c) A readily water-dispersible dispersion concentrate is obtained by mixing 20 parts by weight of the compound of formula I or of an active compound mixture comprising a herbicide and a safener of the formula I, 6 parts by weight of alkylphenol polyglycol ether (®Triton X 207), 3 parts by weight of isotridecanol polyglycol ether (8 EO) and 71 parts. by weight of paraffinic mineral oil (boiling range for example, from about 255 to above 277° C.), and grinding the mixture to a fineness of less than 5 microns in a ball attrition mill.

d) An emulsifiable concentrate is obtained from 15 parts by weight of a compound of the formula I or of an active compound mixture comprising a herbicide and a safener of the formula I, 75 parts by weight of cyclohexanone as solvent and 10 parts by weight of oxyethylated nonylphenol as emulsifier.

e) Water-dispersible granules are obtained by mixing

| 75 parts by weight | of a compound of the formula I or of an active compound mixture comprising a herbicide and a safener of the formula I, |
| --- | --- |
| 10 parts by weight | of calcium ligninsulfonate, |
| 5 parts by weight | of sodium lauryl sulfate, |
| 3 parts by weight | of polyvinyl alcohol and |
| 7 parts by weight | of kaolin, | grinding the mixture in an pin mill, and granulating the powder in a fluidized bed by spraying on water as granulation liquid.

f) Water-dispersible granules are also obtained by homogenizing and precomminuting

| 25 parts by weight | of a compound of the formula I or of an active compound mixture comprising herbicides and a safener of the formula I, |
| --- | --- |
| 5 parts by weight | of sodium 2,2'-dinaphthyl-methane-6,6'-disulfonate |
| 2 parts by weight | of sodium oleoylmethyl-taurate, |
| 1 part by weight | of polyvinyl alcohol, |

-continued

| | |
|---|---|
| 17 parts by weight | of calcium carbonate and |
| 50 parts by weight | of water, | subsequently grinding the mixture in a bead mill, and atomizing the resultant suspension in a spray tower by means of a one-component nozzle and drying it.

B. Preparation Examples

1. Diethyl 2-phenoxymalonate (Example 2 from Table 1): 22.1 g (160 mmol) of potassium carbonate were suspended in 30 ml of acetone, 7.5 g (80 nmol) of phenol in 100 ml of acetone were added, and the mixture was refluxed for 1 hour. 15.5 g (80 mmol) of diethyl 2-chloromalonate in 100 ml of acetone were subsequently added dropwise, the mixture was refluxed for 10 hours and evaporated in vacuo, and the residue was taken up in methylene chloride. The organic phase was washed with saturated NaHCO$_3$ solution and saturated NaCl solution, dried over magnesium sulfate and evaporated. Column chromatography (silica gel, heptane/diethyl ether 2:1) of the residue gave 15.5 g (77% of theory) diethyl 2-phenoxymalonate as a colorless liquid.

2. Ethyl 2-(3,4-dichlorophenoxy)-3-ketobutanoate (Example 38 from Table 1):

13.0 g (80 mmol) of 3,4-dichlorophenol and 12.2 g (88 mmol) of potassium carbonate were refluxed for 30 minutes in 400 ml of acetone. 15.8 g (96 mmol) of ethyl 2-chloroacetoacetate were subsequently added dropwise, the mixture was refluxed for 8 hours and evaporated in vacuo, and water was added to the residue. The aqueous phase was extracted three times with ethyl acetate, and the combined organic phases were dried over magnesium sulfate and evaporated. Column chromatography of the residue gave 15.8 g (68% of theory) of ethyl 2-(3,4-dichlorophenoxy)-3-ketobutanate as an oil.

Tables 1 and 2 below show the abovementioned preparation examples with further examples of compounds of the formula I prepared analogously.

TABLE 1

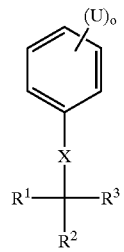

Abbreviations used: Bz = benzyl

| Ex. | X | (U)$_o$ | R$^1$ | R$^2$ | R$^3$ | m.p. [°C.] (n$_D^{30}$) |
|---|---|---|---|---|---|---|
| 1 | O | H | COOH | COO—H | H | |
| 2 | O | H | COO—C$_2$H$_5$ | COO—C$_2$H$_5$ | H | (1.4902) |
| 3 | O | H | COO—C$_2$H$_5$ | COO—CH(CH$_3$)(CH$_2$)$_4$CH$_3$ | H | (1.4765) |
| 4 | O | H | COO—CH(CH$_3$)(CH$_2$)$_4$CH$_3$ | COO—CH(CH$_3$)(CH$_2$)$_4$CH$_3$ | H | (1.4700) |
| 5 | O | 4-Cl | COOH | COOH | H | |
| 6 | O | 4-Cl | COO—C$_2$H$_5$ | COO—C$_2$H$_5$ | H | (1.5000) |
| 7 | O | 4-Cl | COO—C$_2$H$_5$ | COO—CH(CH$_3$)(CH$_2$)$_4$CH$_3$ | H | (1.4869) |
| 8 | O | 4-Cl | COO—CH(CH$_3$)(CH$_2$)$_4$CH$_3$ | COO—CH(CH$_3$)(CH$_2$)$_4$CH$_3$ | H | (1.4790) |
| 9 | O | 4-Cl | COO—CH$_2$CH=CH$_2$ | COO—CH$_2$CH=CH$_2$ | H | |
| 10 | O | 4-Cl | COO—C$_4$H$_9$ (n) | COO—C$_4$H$_9$ (n) | H | |
| 11 | O | 4-Cl | COO—C$_8$H$_{17}$ (i) | COO—C$_8$H$_{17}$ (i) | H | |
| 12 | O | 4-Cl | COOH | COOH | CH$_3$ | |
| 13 | O | 4-Cl | COO—C$_2$H$_5$ | COO—C$_2$H$_5$ | CH$_3$ | (1.4920) |
| 14 | O | 4-Cl | COO—C$_2$H$_5$ | COO—C$_2$H$_5$ | Bz | |
| 15 | O | 4-Cl | COO—C$_2$H$_5$ | CO—CH$_3$ | H | n$_D^{21}$: 1.5162 |
| 16 | O | 4-Cl | COO—CH(CH$_3$)(CH$_2$)$_4$CH$_3$ | CO—CH$_3$ | H | |
| 17 | O | 4-Cl | COO—C$_2$H$_5$ | CO—CH$_2$—C$_6$H$_5$ | H | |
| 18 | O | 4-Cl | COO—C$_2$H$_5$ | C(=NOH)—CH$_3$ | H | |
| 19 | O | 4-Cl | COO—C$_2$H$_5$ | C(OC$_2$H$_5$)$_2$—CH$_3$ | H | |
| 20 | O | 4-Cl | CO—CH$_3$ | CO—CH$_3$ | H | |
| 21 | O | 4-Cl | C(=NOH)—CH$_3$ | C(=NOH)—CH$_3$ | H | |
| 22 | O | 4-Cl | COO—C$_2$H$_5$ | CN | H | |
| 23 | O | 4-Cl | CN | CN | H | |
| 24 | O | 2,4-Cl$_2$ | COOH | COOH | H | |
| 25 | O | 2,4-Cl$_2$ | COO—C$_2$H$_5$ | COO—C$_2$H$_5$ | H | (1.5139) |
| 26 | O | 2,4-Cl$_2$ | COO—C$_2$H$_5$ | COO—CH(CH$_3$)(CH$_2$)$_4$CH$_3$ | H | (1.4931) |
| 27 | O | 2,4-Cl$_2$ | COO—CH(CH$_3$)(CH$_2$)$_4$CH$_3$ | COO—CH(CH$_3$)(CH$_2$)$_4$—CH$_3$ | H | (1.4837) |
| 28 | O | 2,4-Cl$_2$ | COOH | CO—CH$_3$ | H | |
| 29 | O | 2,4-Cl$_2$ | COO—C$_2$H$_5$ | CO—CH$_3$ | H | |
| 30 | O | 2,4-Cl$_2$ | COO—CH(CH$_3$)(CH$_2$)$_4$CH$_3$ | CO—CH$_3$ | H | |
| 31 | O | 2,4-Cl$_2$ | COONa | CO—CH$_3$ | H | |
| 32 | O | 2,4-Cl$_2$ | COOK | CO—CH$_3$ | H | |
| 33 | O | 2,4-Cl$_2$ | COO—C$_2$H$_5$ | CN | H | |
| 34 | O | 2,4-Cl$_2$ | CN | CN | H | |

TABLE 1-continued

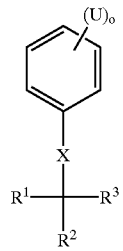

Abbreviations used: Bz = benzyl

| Ex. | X | (U)$_o$ | R$^1$ | R$^2$ | R$^3$ | m.p. [° C.] (n$_D^{30}$) |
|---|---|---|---|---|---|---|
| 35 | O | 2,4-Cl$_2$ | CO—CH$_3$ | CO—CH$_3$ | H | |
| 36 | O | 3,4-Cl$_2$ | COOH | COOH | H | |
| 37 | O | 3,4-Cl$_2$ | COO—C$_2$H$_5$ | COO—C$_2$H$_5$ | H | (1.5117) |
| 38 | O | 3,4-Cl$_2$ | COO—C$_2$H$_5$ | COO—CH(CH$_3$)(CH$_2$)$_4$CH$_3$ | H | (1.4950) |
| 39 | O | 3,4-Cl$_2$ | COO—CH(CH$_3$)(CH$_2$)$_4$—CH$_3$ | COO—CH(CH$_3$)(CH$_2$)$_4$—CH$_3$ | H | (1.4857) |
| 40 | O | 3,4-Cl$_2$ | COO—C$_2$H$_5$ | CO—CH$_3$ | H | n$_D^{21}$: 1.5131 |
| 41 | O | 3,4-Cl$_2$ | COO—CH(CH$_3$)(CH$_2$)$_4$—CH$_3$ | CO—CH$_3$ | H | |
| 42 | O | 3,4-Cl$_2$ | COO—C$_2$H$_5$ | C(OC$_2$H$_5$)$_2$—CH$_3$ | H | |
| 43 | O | 3,4-Cl$_2$ | CN | CN | H | |
| 44 | O | 3,4-Cl$_2$ | CN | COO—C$_2$H$_5$ | H | |
| 45 | O | 2-CH$_3$, 4-Cl | COOH | COOH | H | |
| 46 | O | 2-CH$_3$, 4-Cl | COO—C$_2$H$_5$ | COO—C$_2$H$_5$ | H | |
| 47 | O | 2-CH$_3$, 4-Cl | COO—C$_2$H$_5$ | COO—CH(CH$_3$)(CH$_2$)$_4$CH$_3$ | H | |
| 48 | O | 2-CH$_3$, 4-Cl | COO—CH(CH$_3$)(CH$_2$)$_4$—CH$_3$ | COO—CH(CH$_3$)(CH$_2$)$_4$—CH$_3$ | H | |
| 49 | O | 2-CH$_3$, 4-Cl | COO—C$_2$H$_5$ | CO—CH$_3$ | H | |
| 50 | O | 4-F | COO—C$_2$H$_5$ | COO—C$_2$H$_5$ | H | |
| 51 | O | 4-F | COO—C$_2$H$_5$ | COO—CH(CH$_3$)(CH$_2$)$_4$CH$_3$ | H | |
| 52 | O | 4-F | COO—CH(CH$_3$)(CH$_2$)$_4$—CH$_3$ | COO—CH(CH$_3$)(CH$_2$)$_4$—CH$_3$ | H | |
| 53 | O | 4-F | COO—C$_2$H$_5$ | CO—CH$_3$ | H | |
| 54 | O | 4-Br | COOH | COOH | H | |
| 55 | O | 4-Br | COO—C$_2$H$_5$ | COO—C$_2$H$_5$ | H | (1.5160) |
| 56 | O | 4-Br | COO—C$_2$H$_5$ | COO—CH(CH$_3$)(CH$_2$)$_4$CH$_3$ | H | (1.4969) |
| 57 | O | 4-Br | COO—CH(CH$_3$)$_2$(CH$_2$)$_4$—CH$_3$ | COO—CH(CH$_3$(CH$_2$)$_4$—CH$_3$ | H | (1.4877) |
| 58 | O | 4-Br | COO—C$_2$H$_5$ | COO—C$_2$H$_5$ | CH$_3$ | |
| 59 | O | 4-Br | COO—C$_2$H$_5$ | CO—CH$_3$ | H | (1.5321) |
| 60 | O | 4-Br | COO—CH(CH$_3$)(CH$_2$)$_4$—CH$_3$ | CO—CH$_3$ | H | |
| 61 | O | 4-Br | CO—CH$_3$ | CO—CH$_3$ | H | |
| 62 | O | 4-Br | CN | COO—C$_2$H$_5$ | H | |
| 63 | O | 4-Br | CN | CN | H | |
| 64 | O | 4-CH$_3$ | COO—C$_2$H$_5$ | COO—C$_2$H$_5$ | H | |
| 65 | O | 4-CH$_3$ | COO—CH(CH$_3$)(CH$_2$)$_4$—CH$_3$ | COO—CH(CH$_3$)(CH$_2$)$_4$—CH$_3$ | H | |
| 66 | O | 4-OC$_2$H$_5$ | COO—C$_2$H$_5$ | COO—C$_2$H$_5$ | H | |
| 67 | O | 4-OC$_2$H$_5$ | COO—CH(CH$_3$)(CH$_2$)$_4$—CH$_3$ | COO—CH(CH$_3$)(CH$_2$)$_4$—CH$_3$ | H | |
| 68 | O | 2-Cl, 4-CF$_3$ | COOH | COOH | H | |
| 69 | O | 2-Cl, 4-CF$_3$ | COO—C$_2$H$_5$ | COO—C$_2$H$_5$ | H | |
| 70 | O | 2-Cl, 4-CF$_3$ | COO—C$_2$H$_5$ | COO—CH(CH$_3$)(CH$_2$)$_4$—CH$_3$ | H | |
| 71 | O | 2-Cl, 4-CF$_3$ | COO—CH(CH$_3$)(CH$_2$)$_4$—CH$_3$ | COO—CH(CH$_3$)(CH$_2$)$_4$—CH$_3$ | H | |
| 72 | O | 2-Cl, 4-CF$_3$ | COO—C$_2$H$_5$ | CO—CH$_3$ | H | |
| 73 | O | 3-Br | COO—C$_2$H$_5$ | COO—C$_2$H$_5$ | H | |
| 74 | O | 3-I | COO—C$_2$H$_5$ | COO—C$_2$H$_5$ | H | |
| 75 | O | 2-F | COO—C$_2$H$_5$ | COO—C$_2$H$_5$ | H | |
| 76 | O | 2-Cl | COO—C$_2$H$_5$ | COO—C$_2$H$_5$ | H | |
| 77 | O | 2-Cl | COO—CH(CH$_3$)(CH$_2$)$_4$—CH$_3$ | COO—CH(CH$_3$)(CH$_2$)$_4$—CH$_3$ | H | |
| 78 | O | 2-Cl | COO—C$_2$H$_5$ | CO—CH$_3$ | H | |
| 79 | O | 4-NO$_2$ | COO—C$_2$H$_5$ | COO—C$_2$H$_5$ | H | |
| 80 | O | 2-NO$_2$ | COO—C$_2$H$_5$ | COO—C$_2$H$_5$ | H | |
| 81 | O | 2-NO$_2$, 4-Cl | COOH | COOH | H | |
| 82 | O | 2-NO$_2$, 4-Cl | COO—C$_2$H$_5$ | COO—C$_2$H$_5$ | H | |
| 83 | O | 2-NO$_2$, 4-Cl | COO—C$_2$H$_5$ | COO—CH(CH$_3$)(CH$_2$)$_4$—CH$_3$ | H | |
| 84 | O | 2-NO$_2$, 4-Cl | COO—CH(CH$_3$)(CH$_2$)$_4$—CH$_3$ | COO—CH(CH$_3$)(CH$_2$)$_4$—CH$_3$ | H | |
| 85 | O | 2-NO$_2$, 4-Cl | COO—C$_2$H$_5$ | CO—CH$_3$ | H | |
| 86 | O | 2-NO$_2$, 4-Cl | COO—C$_2$H$_5$ | C(NOH)—CH$_3$ | H | |
| 87 | O | 2-NO$_2$, 4-Cl | CN | CN | H | |
| 88 | O | 2-NO$_2$, 4-Cl | COO—C$_2$H$_5$ | CN | H | |
| 89 | O | 2-NH$_2$, 4-Cl | COO—C$_2$H$_5$ | COO—C$_2$H$_5$ | H | |
| 90 | O | 2-N(CH$_3$)$_2$, 4-Cl | COO—C$_2$H$_5$ | COO—C$_2$H$_5$ | H | |
| 91 | S | H | COO—C$_2$H$_5$ | COO—C$_2$H$_5$ | H | |
| 92 | S | 4-Cl | COO—C$_2$H$_5$ | COO—C$_2$H$_5$ | H | b.p. (0.1) 140–145° |

TABLE 1-continued

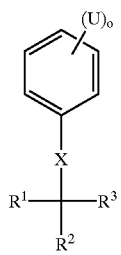

Abbreviations used: Bz = benzyl

| Ex. | X | (U)$_o$ | R$^1$ | R$^2$ | R$^3$ | m.p. [° C.] (n$_D^{30}$) |
|---|---|---|---|---|---|---|
| 93 | S | 4-Cl | CN | CN | H | |
| 94 | S | 4-Br | COO—C$_2$H$_5$ | COO—C$_2$H$_5$ | H | |
| 95 | S | 2,5-Cl$_2$ | COO—C$_2$H$_5$ | COO—C$_2$H$_5$ | H | |
| 96 | NH | 4-Cl | COO—C$_2$H$_5$ | COO—C$_2$H$_5$ | H | 94–95 |
| 97 | NH | 2,4-Cl$_2$ | COO—C$_2$H$_5$ | COO—C$_2$H$_5$ | H | |
| 98 | NH | 3-Cl | COO—C$_2$H$_5$ | COO—C$_2$H$_5$ | H | |
| 99 | NH | 3,4-Cl$_2$ | COO—C$_2$H$_5$ | COO—C$_2$H$_5$ | H | |
| 100 | NCH$_3$ | | COO—C$_2$H$_5$ | COO—C$_2$H$_5$ | H | |
| 101 | NCH(CH$_3$)$_2$ | 4-Cl | COO—C$_2$H$_5$ | COO—C$_2$H$_5$ | H | |
| 102 | NCH(CH$_3$)$_2$ | 4-Cl | COO—C$_2$H$_5$ | COO—CH(CH$_3$)(CH$_2$)$_4$—CH$_3$ | H | |
| 103 | NCH(CH$_3$)$_2$ | 4-Cl | COO—CH(CH$_3$)(CH$_2$)$_4$—CH$_3$ | COO—CH(CH$_3$)(CH$_2$)$_4$—CH$_3$ | H | |
| 104 | NH—NH | 4-Cl | COO—C$_2$H$_5$ | COO—C$_2$H$_5$ | H | |
| 105 | NH—NH | 3,4-Cl$_2$ | COO—C$_2$H$_5$ | COO—C$_2$H$_5$ | H | |
| 106 | NH—NH | 2,4-Cl$_2$ | COO—C$_2$H$_5$ | COO—C$_2$H$_5$ | H | |
| 107 | NH—NH | 4-Br | COO—C$_2$H$_5$ | COO—C$_2$H$_5$ | H | |
| 108 | O | 3-Cl | COO—C$_2$H$_5$ | CO—CH$_3$ | H | |
| 109 | O | 3-Cl | COO—C$_2$H$_5$ | COO—C$_2$H$_5$ | H | (1.5016) |
| 110 | O | 3-Cl | COO—C$_2$H$_5$ | COO—CH(CH$_3$)(CH$_2$)$_4$—CH$_3$ | H | (1.4838) |
| 111 | O | 3-Cl | COO—CH(CH$_3$)(CH$_2$)$_4$—CH$_3$ | COO—CH(CH$_3$)(CH$_2$)$_4$—CH$_3$ | H | (1.4779) |
| 112 | O | 3-Cl | COO—C$_2$H$_5$ | CN | H | |
| 113 | O | 3-Cl | CN | CN | H | |
| 114 | O | 4-O-(6-chlorobenzoxazol-2-yl) | COO—C$_2$H$_5$ | COO—C$_2$H$_5$ | H | resin |
| 115 | O | — | COOC$_2$H$_5$ | COOC$_2$H$_5$ | CH$_3$ | oil |
| 116 | S | 4-Cl | COOC$_2$H$_5$ | COOC$_2$H$_5$ | SC$_6$H$_4$-p-Cl | 77–80 |

TABLE 2

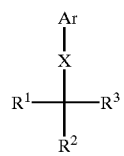

| Ex. | Ar | X | R$^1$ | R$^2$ | R$^3$ | m.p. [° C.] (n$_D^{30}$) |
|---|---|---|---|---|---|---|
| 1 | 2-methylpyridinyl | O | COOH | COOH | H | |
| 2 | " | O | COO—C$_2$H$_5$ | COO—C$_2$H$_5$ | H | |
| 3 | " | O | COO—CH(CH$_3$)(CH$_2$)$_4$—CH$_3$ | COO—CH(CH$_3$)(CH$_2$)$_4$—CH$_3$ | H | |
| 4 | " | O | COO—CH$_2$—CH=CH$_2$ | COO—CH$_2$—CH=CH$_2$ | H | |
| 5 | " | O | COO—C$_4$H$_9$ (n) | COO—C$_4$H$_9$ (n) | H | |
| 6 | " | O | COO—C$_8$H$_{17}$ (i) | COO—C$_8$H$_{17}$ (i) | H | |
| 7 | " | O | COO—C$_2$H$_5$ | COO—C$_2$H$_5$ | CH$_3$ | |
| 8 | " | O | COO—C$_2$H$_5$ | CO—CH$_3$ | H | |
| 9 | " | O | COO—CH(CH$_3$)(CH$_2$)$_4$—CH$_3$ | CO—CH$_3$ | H | |

TABLE 2-continued $$\begin{array}{c} Ar \\ | \\ X \\ | \\ R^1 - C - R^3 \\ | \\ R^2 \end{array}$$

| Ex. | Ar | X | R¹ | R² | R³ | m.p. [° C.] ($n_D^{30}$) |
|---|---|---|---|---|---|---|
| 10 | " | O | CH₃ CN | CN | H | |
| 11 | " | O | COO—C₂H₅ | CN | H | |
| 12 | 4-Cl-2-methylpyridin-yl | O | COOH | COOH | H | |
| 13 | " | O | COO—C₂H₅ | COO—C₂H₅ | H | |
| 14 | " | O | COO—CH(CH₃)(CH₂)₄—CH₃ | COO—CH(CH₃)(CH₂)₄—CH₃ | H | |
| 15 | " | O | COO—C₂H₅ | CO—CH₃ | H | |
| 16 | " | O | CN | CN | H | |
| 17 | " | O | COO—C₂H₅ | CN | H | |
| 18 | 8-methylquinolin-yl | O | COOH | COOH | H | 147 (decomp.) |
| 19 | " | O | COO—C₂H₅ | COO—C₂H₅ | H | (1.5370) |
| 20 | " | O | COO—C₂H₅ | COO—CH(CH₃)(CH₂)₄—CH₃ | H | (1.5205) |
| 21 | " | O | COO—CH(CH₃)(CH₂)₄—CH₃ | COO—CH(CH₃)(CH₂)₄—CH₃ | H | (1.5045) |
| 22 | " | O | COO—CH₂—CH=CH₂ | COO—CH₂—CH=CH₂ | H | |
| 23 | " | O | COO—C₂H₅ | CO—CH₃ | H | $n_D^{21}$: 1.5570 |
| 24 | " | O | COO—CH(CH₃)(CH₂)₄—CH₃ | CO—CH₃ | H | oil |
| 25 | " | O | COO—C₂H₅ | CN | H | |
| 26 | " | O | CN | CN | H | |
| 27 | 5-Cl-8-methylquinolin-yl | O | COOH | COOH | H | 226 |
| 28 | " | O | COO—C₂H₅ | COO—C₂H₅ | H | 77–78 |
| 29 | " | O | COO—C₂H₅ | COO—CH(CH₃)(CH₂)₄—CH₃ | H | |
| 30 | " | O | COO—CH(CH₃)(CH₂)₄—CH₃ | COO—CH(CH₃)(CH₂)₄—CH₃ | H | (1.5145) |
| 31 | " | O | COO—CH₂—CH=CH₂ | COO—CH₂—CH=CH₂ | H | (1.5597) |
| 32 | " | O | COO—CH(CH₃)₂ | COO—CH(CH₃)₂ | H | (1.5344) |
| 33 | " | O | COO—C₄H₉ (n) | COO—C₄H₉ (n) | H | |
| 34 | " | O | COO—C₂H₅ | COO—C₄H₉ (t) | H | |
| 35 | " | O | COO—C₄H₉ (t) | COO—C₄H₉ (t) | H | |
| 36 | " | O | COO—C₈H₁₇ (i) | COO—C₈H₁₇ (i) | H | |
| 37 | " | O | COO—C₂H₅ | COO—C₅H₉ (c) | H | |
| 38 | " | O | COO—C₅H₉ (c) | COO—C₅H₉ (c) | H | (1.5519) |
| 39 | " | O | COO—CH₂C₆H₅ | COO—CH₂C₆H₅ | H | resin |
| 40 | " | O | COO—CH₂CH₂OH | COO—CH₂CH₂OH | H | |
| 41 | " | O | COO—CH₂CF₃ | COO—CH₂CF₃ | H | |
| 42 | " | O | COOH | COOH | CH₃ | |
| 43 | " | O | COO—C₂H₅ | COO—C₂H₅ | CH₃ | |
| 44 | " | O | COO—C₂H₅ | COO—CH(CH₃)(CH₂)₄—CH₃ | CH₃ | |

TABLE 2-continued

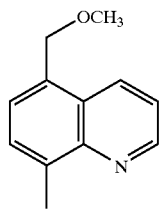

| Ex. | Ar | X | R¹ | R² | R³ | m.p. [° C.] ($n_D^{30}$) |
|---|---|---|---|---|---|---|
| 45 | " | O | COO—CH(CH₃)(CH₂)₄—CH₃ | COO—CH(CH₃)(CH₂)₄—CH₃ | CH₃ | |
| 46 | " | O | COOH | COOH | Bz | |
| 47 | " | O | COO—C₂H₅ | COO—C₂H₅ | Bz | |
| 48 | " | O | COO—C₂H₅ | COO—CH(CH₃)(CH₂)₄—CH₃ | Bz | |
| 49 | " | O | COO—CH(CH₃)(CH₂)₄—CH₃ | COO—CH(CH₃)(CH₂)₄—CH₃ | Bz | |
| 50 | " | O | COO—C₂H₅ | CO—CH₃ | H | $n_D^{21}$: 1.5100 |
| 51 | " | O | COO—CH(CH₃)(CH₂)₄—CH₃ | CO—CH₃ | H | (1.5350) |
| 52 | " | O | COO—C₂H₅ | C(NOH)—CH₃ | H | |
| 53 | " | O | COO—C₂H₅ | C(OC₂H₅)₂—CH₃ | H | |
| 54 | " | O | COO—C₂H₅ | CN | H | |
| 55 | " | O | CN | CN | H | |
| 56 | 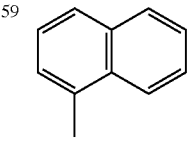 | O | COO—C₂H₅ | COO—C₂H₅ | H | oil |
| 57 | " | O | COO—C₂H₅ | COO—CH(CH₃)(CH₂)₄—CH₃ | H | resin |
| 58 | " | O | COO—CH(CH₃)(CH₂)₄—CH₃ | COO—CH(CH₃)(CH₂)₄—CH₃ | H | resin |
| 59 | 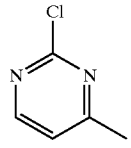 | O | COO—C₂H₅ | COO—C₂H₅ | H | (1.5508) |
| 60 | " | O | COO—C₂H₅ | CO—CH₃ | H | |
| 61 | 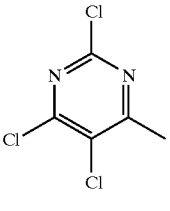 | O | COO—C₂H₅ | COO—C₂H₅ | H | oil |
| 62 | 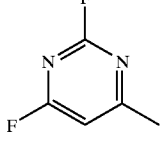 | O | COO—C₂H₅ | COO—C₂H₅ | H | oil |
| 63 |  | O | COO—C₂H₅ | COO—C₂H₅ | H | oil |

TABLE 2-continued

Ar—X—C(R¹)(R²)(R³)

| Ex. | Ar | X | R¹ | R² | R³ | m.p. [° C.] ($n_D^{30}$) |
|---|---|---|---|---|---|---|
| 64 | 2,4-dichloro-6-methylpyrimidin-5-yl | O | COO—C₂H₅ | COO—C₂H₅ | H | oil |
| 65 | 2,5-dichloro-4-methylpyrimidin-6-yl | O | COO—C₂H₅ | COO—C₂H₅ | H | (1.5078) |
| 66 | 2-chloro-6-methyl-1,3,5-triazin-4-yl | O | COO—C₂H₅ | COO—C₂H₅ | H | (1.4890) |
| 67 | 8-methylquinolin-2-yl | S | COO—C₂H₅ | COO—C₂H₅ | H | oil |
| 68 | " | O | COO—CH₃ | COO—C₂H₅ | H | (1.5558) |
| 69 | 5-bromo-8-methylquinolin-2-yl | O | COO—C₂H₅ | COO—C₂H₅ | H | 82–83 |
| 70 | 5-chloro-8-methylquinolin-2-yl | O | COO—CH₃ | COO—CH₃ | H | 88.5 |
| 71 | " | O | COO—CH₃ | COO—C₂H₅ | H | (1.5486) |
| 72 | " | O | COO—CH₃ | COO—C₂H₅ | CH₃ | |
| 73 | " | O | COO—CH₃ | COO—C₂H₅ | Br | |
| 74 | " | O | COO—CH₃ | COO—C₂H₅ | C₂H₅ | |
| 75 | " | O | COO—C₂H₅ | COO—CH₂—CH=CH₂ | H | oil |
| 76 | " | O | COO—CH₂—CH=CH₂ | COO—CH₂—CH=CH₂ | CH₃ | |
| 77 | " | O | COO—C₃H₇ | COO—C₃H₇ | H | |
| 78 | " | O | COO—CH₂CCl₃ | COO—CH₂—CCl₃ | H | |
| 79 | " | O | COO—CH₂CH₂Cl | COO—CH₂CH₂Cl | H | |
| 80 | " | O | COO—C₅H₁₁ (n) | COO—C₅H₁₁ (n) | H | |

TABLE 2-continued

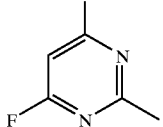

| Ex. | Ar | X | R$^1$ | R$^2$ | R$^3$ | m.p. [° C.] (n$_D^{30}$) |
|---|---|---|---|---|---|---|
| 81 | 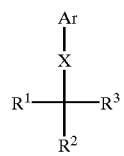 | O | COO—C$_2$H$_5$ | COO—C$_2$H$_5$ | H | oil |

Abbreviations used: Bz = benzyl

C. Biological examples

Example 1

Seeds of wheat and barley were placed in sandy loam soil in plastic pots, raised to the 3- to 4-leaf stage in a greenhouse and then treated successively with the compounds according to the invention and the herbicides using the post-emergence method. The herbicides and the compounds of the formula I were applied in the form of aqueous suspensions or emulsions at an application rate of 300 l/ha (converted). 3–4 weeks after the treatment, the plants were assessed visually for damage of any type caused by the herbicides applied, in particular the extent of lasting growth inhibition being taken into account. The assessment was made in percentages compared with untreated controls. Some experimental results are shown in Tables 3 and 4.

TABLE 3

Safener action on wheat and barley

| Active compound | Application rate [g of a.i./ha] herbicide | safener | Damage [%] TA | HV | TD |
|---|---|---|---|---|---|
| H1 | 400 | — | 40 | 98 | 98 |
|  | 200 | — | 30 | 90 | 95 |
|  | 100 | — | 10 | 80 | 95 |
| H1 + | 400 | 50 | 10 | 20 | 10 |
| Ex. 28/Tab 2 | 200 | 25 | 0 | 0 | 0 |
|  | 100 | 12 | 0 | 0 | 0 |
| H6 + | 400 | 50 | 10 | 25 | 15 |
| Ex. 31/Tab 2 | 200 | 25 | 0 | 15 | 0 |
|  | 100 | 12 | 0 | 0 | 0 |
| H6 + | 400 | 100 | 15 | 25 | 20 |
| Ex. 27/Tab 2 | 200 | 50 | 0 | 10 | 5 |
|  | 100 | 25 | 0 | 0 | 0 |
| H2 | 1800 | — | — | 40 | — |
|  | 900 | — | — | 10 | — |
| H2 + | 1800 | 225 | — | 0 | — |
| Ex. 71/Tab 2 | 900 | 112 | — | 0 | — |
| H3 | 50 | — | 70 | 60 | — |
|  | 25 | — | 80 | 30 | — |
|  | 12 | — | 15 | 20 | — |
| H3 + | 50 | 25 | 20 | 10 | — |
| Ex. 28/Tab 2 | 25 | 12 | 10 | 5 | — |
|  | 12 | 6 | 0 | 0 | — |
| H3 + | 50 | 25 | 15 | 10 | — |
| Ex. 71/Tab 2 | 25 | 12 | 0 | 0 | — |
|  | 12 | 6 | 0 | 0 | — |
| H3 + | 50 | 25 | 25 | 20 | — |
| Ex. 75/Tab 2 | 25 | 12 | 5 | 5 | — |
|  | 12 | 6 | 0 | 0 | — |
| H3 + | 50 | 25 | 25 | 20 | — |
| Ex. 31/Tab 2 | 25 | 12 | 15 | 10 | — |
|  | 12 | 6 | 0 | 0 | — |

Key to Table 3:
Test conditions: Application at the 4-leaf stage; assessment after 4 weeks; 4 replications
Abbreviations:
 H1=fenoxaprop-P-ethyl
 H2=diclofop-methyl
 H3=methyl 4-iodo-2-[3-(4-methoxy-6-methyl-1,3,5-triazin-2-yl)ureidosulfonyl]benzoate, sodium salt
 HV=Hordeum vulgare (barley)
 TA=Triticum aestivum (wheat)
 TD=Triticum durum (hard wheat)
 Ex. No./Tab No.=safener No. from Table No.
 —=not applied (in the case of safeners) or not tested (in the case of plant crops)

TABLE 4

Safener action on barley

| Active component | Application rate [g of a.i./ha] herbicide | safener | Damage [%] HV |
|---|---|---|---|
| H1 | 200 | — | 85 |
| H1 + Ex. 27/Tab 2 | 200 | 1250 | 50 |
| H1 + Ex. 30/Tab 2 | 200 | 1250 | 65 |
| H1 + Ex. 50/Tab 2 | 200 | 1250 | 30 |
| H1 + Ex. 64/Tab 2 | 200 | 1250 | 35 |
| H1 + Ex. 70/Tab 2 | 200 | 1250 | 30 |
| H1 + Ex. 32/Tab 2 | 200 | 1250 | 50 |
| H1 + Ex. 75/Tab 2 | 200 | 1250 | 33 |

TABLE 4-continued

Safener action on barley

| Active component | Application rate [g of a.i./ha] herbicide | safener | Damage [%] HV |
|---|---|---|---|
| H1 + Ex. 39/Tab 2 | 200 | 1250 | 25 |
| H1 + Ex. 19/Tab 2 | 200 | 1250 | 60 |
| H1 + Ex. 51/Tab 2 | 200 | 1250 | 50 |

Test conditions: Application at the 3-leaf stage; assessment after 2–3 weeks; 4 replications
Abbreviations: see abbreviations for Table 3

Even when the herbicide is applied in very excessive amounts, severe damage to the crop plants is significantly reduced, and slight damage is completely eliminated.

Mixture of herbicides and compounds according to the invention are therefore highly suitable for selective weed control in cereal crops.

EXAMPLE 2

Corn plants, weed and weed grasses were raised to the 4- to 5-leaf stage in plastic pots outside or in the greenhouse and treated successively with herbicides and compounds of the formula I according to the invention using the post-emergence method. The active compounds were applied in the form of aqueous suspensions or emulsions and an application rate of 300 l of water/ha (converted). 4 weeks after the treatment, the plants were assessed visually for any type of damage caused by the herbicides applied, in particular the extent of lasting growth inhibition being taken into account. The assessment was made in percent compared with untreated controls. Some results are shown in Tables 5 to 7.

TABLE 5

Safener action on corn (Zea mays)

| Active compound(s) | Application rate [g of a.i./ha] herbicide | safener | Damage to corn [%] Alois variety | Felix variety |
|---|---|---|---|---|
| H4 | 300 | — | 60 | 60 |
|  | 150 | — | 55 | 50 |
|  | 75 | — | 40 | 30 |
|  | 38 | — | 20 | 0 |
| H4 + Ex. 28/Tab 2 | 300 | 150 | 30 | 25 |
|  | 150 | 75 | 10 | 15 |
|  | 75 | 38 | 0 | 0 |
|  | 38 | 19 | 0 | 0 |
| H4 + Ex. 31/Tab 2 | 300 | 150 | 40 | 30 |
|  | 150 | 75 | 15 | 10 |
|  | 75 | 38 | 0 | 0 |
|  | 38 | 19 | 0 | 0 |
| H5 | 200 | — | 50 | 45 |
|  | 100 | — | 40 | 35 |
|  | 50 | — | 30 | 25 |
| H5 + Ex. 28/Tab 2 | 200 | 100 | 20 | 15 |
|  | 100 | 50 | 10 | 5 |
|  | 50 | 25 | 0 | 0 |
| H5 + Ex. 71/Tab 2 | 200 | 100 | 20 | 20 |
|  | 100 | 50 | 5 | 10 |
|  | 50 | 25 | 0 | 0 |

Test conditions: Application at the 4-leaf stage; assessment after 4 weeks; 4 replications
Abbreviations: see Table 3, and H4=benzyl 3-(4,6-dimethoxypyrimidin-2-yloxy)pyridine-2-carboxylate H5=5-ethyl-2-(4-isopropyl-4-methyl-5-oxo-2-imidazolin-2-yl)pyridine-3-carboxylic acid (imazethapyr)

TABLE 6

Safener action on corn (Zea mays)

| Active compound(s) | Application rate [g of a.i./ha] herbicide | safener | Damage [%] in corn varieties Mutin | Felix | Dea |
|---|---|---|---|---|---|
| H6 | 80 | — | 40 | 5 | — |
|  | 40 | — | 20 | 5 | — |
|  | 20 | — | 5 | 10 | — |
| H6 + Ex. 71/Tab 2 | 80 | 40 | 10 | 5 | — |
|  | 40 | 20 | 0 | 0 | — |
|  | 20 | 10 | 0 | 0 | — |
| H6 + Ex. 70/Tab 2 | 80 | 40 | 20 | 15 | — |
|  | 40 | 20 | 5 | 0 | — |
|  | 20 | 10 | 0 | 0 | — |
| H7 | 60 | — | 70 | 75 | — |
|  | 30 | — | 30 | 40 | — |
|  | 15 | — | 10 | 15 | — |
|  | 8 | — | 5 | 0 | — |
| H7 + Ex. 71/Tab 2 | 60 | 30 | 20 | 25 | — |
|  | 30 | 15 | 5 | 10 | — |
|  | 15 | 7.5 | 0 | 0 | — |
|  | 8 | 4 | 0 | 0 | — |
| H7 + Ex. 70/Tab 2 | 60 | 30 | 25 | 25 | — |
|  | 30 | 15 | 10 | 5 | — |
|  | 15 | 7.5 | 0 | 0 | — |
|  | 8 | 4 | 0 | 0 | — |
| H8 | 200 | — | 65 | 70 | 35 |
|  | 100 | — | 60 | 65 | 10 |
|  | 50 | — | 30 | 55 | 0 |
|  | 25 | — | 15 | 25 | 0 |
| H8 + Ex. 31/Tab 2 | 200 | 100 | 40 | 25 | 0 |
|  | 100 | 50 | 20 | 10 | 0 |
|  | 50 | 25 | 0 | 0 | 0 |
|  | 25 | 12 | 0 | 0 | 0 |
| H8 + Ex. 71/Tab 2 | 200 | 100 | 35 | 30 | 5 |
|  | 100 | 50 | 15 | 10 | 0 |
|  | 50 | 25 | 0 | 0 | 0 |
|  | 25 | 12 | 0 | 0 | 0 |
| H8 + Ex. 75/Tab 2 | 200 | 100 | 30 | 30 |  |
|  | 100 | 50 | 20 | 10 | 0 |
|  | 50 | 25 | 0 | 0 | 0 |
|  | 25 | 12 | 0 | 0 | 0 |
| H8 + Ex. 28/Tab 2 | 200 | 100 | 30 | 30 | 0 |
|  | 100 | 50 | 20 | 10 | 0 |
|  | 50 | 25 | 0 | 0 | 0 |
|  | 25 | 12 | 0 | 0 | 0 |

Test conditions: Application at the 4-leaf stage; assessment after 4 weeks; 4 replications.

Abbreviations: see Table 3, and as follows

H6=1-(3-ethylsulfonylpyridin-2-ylsulfonyl)-3-(4,6-dimethoxypyrimidin-2-yl)urea (DPX-E 9636, rimsulfuron)

H7=1-(2-methoxycarbonylthiophen-3-yl)-3-(4-methoxy-6-methyl-1,3,5-triazin-2-yl)urea (thifensulfuron-methyl)

H8=3-(4,6-dimethoxypyrimidin-2-yl)-1-[3(-N-methyl-N-methylsulfonylamino)-2-pyridylsulfonyl]urea

TABLE 7

Safener action on corn (Zea mays)

| Active | Application rate [g of a.i./ha] | | Damage in corn [%] |
|---|---|---|---|
| compound(s) | herbicide | safener | Felix variety |
| H8 | 75 | — | 75 |
| H8 + Ex. 50/Tab 2 | 75 | 1250 | 55 |
| H8 + Ex. 68/Tab 2 | 75 | 1250 | 20 |
| H8 + Ex. 70/Tab 2 | 75 | 1250 | 55 |
| H8 + Ex. 19/Tab 2 | 75 | 1250 | 30 |

Test conditions: Application at the 3-leaf stage; assessment after 3 weeks; 4 replications
Abbreviations: as in Table 6

The results show that the compounds of the formula I according to the invention employed can effectively reduce severe herbicide damage to the corn plants. Even if the herbicides are applied in very excessive amounts, severe damage to the crop plants is significantly reduced and slight damage eliminated completely. Mixtures of herbicides and compounds of the formula I are therefore highly suitable for selective weed control in corn.

EXAMPLE 3

Rice was sown in plastic pots and raised in a greenhouse under optimum growth conditions. After emergence, the pots were filled with water to 2 cm from the top, and this flooding level was maintained throughout the experiment. At the 3- to 4-leaf stage, the plants were then treated with the herbicides and the compounds of the formula I. 3 weeks after treatment, the plants were assessed for damage of any type caused by the herbicides, in particular the extent of lasting growth inhibition and thinning being considered. The results of the assessments show that the safeners effectively reduce herbicide damage to rice. Some results are shown in Table 8.

TABLE 8

Safener action on rice

| Active | Application rate [g of a.i./ha] | | Damage [%] |
|---|---|---|---|
| compound(s) | herbicide | safener | ORSA |
| H1 | 300 | — | 80 |
| H1 + Ex. 28/Tab 2 | 300 | 1250 | 35 |
| H1 + Ex. 27/Tab 2 | 300 | 1250 | 70 |
| H1 + Ex. 30/Tab 2 | 300 | 1250 | 45 |
| H1 + Ex. 50/Tab 2 | 300 | 1250 | 70 |
| H1 + Ex. 64/Tab 2 | 300 | 1250 | 70 |
| H1 + Ex. 70/Tab 2 | 300 | 1250 | 70 |
| H1 + Ex. 32/Tab 2 | 300 | 1250 | 35 |
| H1 + Ex. 75/Tab 2 | 300 | 1250 | 30 |
| H1 + Ex. 31/Tab 2 | 300 | 1250 | 50 |
| H1 + Ex. 39/Tab 2 | 300 | 1250 | 70 |
| H1 + Ex. 19/Tab 2 | 300 | 1250 | 45 |
| H1 + Ex. 51/Tab 2 | 300 | 1250 | 70 |
| H1 + Ex. 71/Tab 2 | 300 | 1250 | 40 |

Test conditions: Application at the 3-leaf stage; assessment after 3 weeks; 4 replications.
Abbreviations: see Table 3 and
ORSA=Oryza sativa (rice)

Mixes of herbicides and the safeners according to the invention are thus suitable for selective weed control in rice. The herbicidal activity of the herbicides employed against weeds are not impaired by addition of the safeners according to the invention; at the application rates used, it corresponds to the comparative values achieved using the herbicides alone.

EXAMPLE 4

Rice was sown in sandy soil in pots in a greenhouse and raised to a growth height of 24–25 cm. The rice was then transplanted into a water-covered soil and, 3 days after transplanting, treated with a herbicide or a herbicide/safener combination by watering. 4 weeks after application, plant damage was assessed visually compared with untreated controls (results see Table 9).

TABLE 9

Safener action on transplanted rice

| Active | Application rate [g of a.i./ha] | | Damage [%] |
|---|---|---|---|
| compound(s) | herbicide | safener | ORSA-T |
| H9 | 450 | — | 50 |
| H9 + Ex. 28/Tab 2 | 450 | 225 | 33 |
| | 450 | 450 | 33 |

Abbreviations as in Table 3, and as follows:
ORSA-T=Oryza sativa (transplanted)
H9=anilofos The example of Table 3 illustrates the safener action of compounds of formula (I) in a herbicide which is structurally completely different from herbicides H1 to H8.

What is claimed is:

1. A compound of the formula I or salts thereof

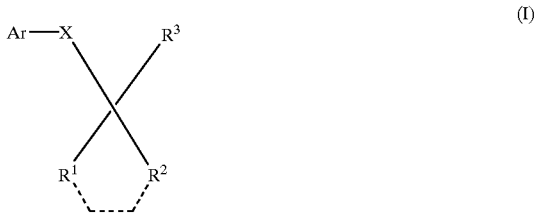

(I)

in which
$R^1$ is a radical of the formula —CN or

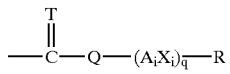

in which R, T, Q, A, X, I and q are defined below, and
$R^2$ is a radical of the formula

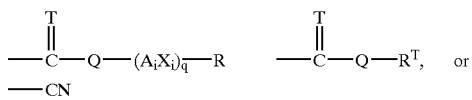

in which R, R T, Q, $A_i$, Xi and q are as defined below, or
$R^1$ and $R^2$ are bonded to one another and together are a group of the formula

—CO—Q$^1$—D—Q$^2$—CO— in which
- Q$^1$ and Q$^2$, independently of one another, are as defined for Q and
- D is a divalent group of the formula CR'R" or C=O, where R' and R", independently of one another, are hydrogen or C$_1$–C$_4$-alkyl, R$^3$ is hydrogen, halogen, C$_1$–C$_{18}$-alkyl, C$_2$–C$_8$-alkenyl, C$_2$–C$_8$-alkynyl, C$_1$–C$_{18}$-alkoxy, C$_2$–C$_8$-alkenyloxy, C$_2$–C$_8$-alkynyloxy, C$_1$–C$_{18}$-alkylthio, C$_2$–C$_8$-alkenylthio, C$_2$–C$_8$-alkynylthio, where each of the 9 last-mentioned radicals is in each case unsubstituted or substituted by one or more radicals from the group consisting of halogen, nitro and cyano, or is C$_3$–C$_{12}$-cycloalkyl which is unsubstituted or substituted by one or more radicals from the group consisting of C$_1$–C$_4$-alkyl, halogen, nitro and cyano, or is SiR$^a$R$^b$R$^c$, in which R$^a$, R$^b$ and R$^c$, independently of one another, are C$_1$–C$_4$-alkyl, C$_2$–C$_4$-alkenyl, C$_2$–C$_4$-alkynyl or substituted or unsubstituted phenyl, or is a radical of the formula Ar'X'—, in which Ar' and X' are defined analogously to Ar and X, X is O, S, NH—NH or NR$^d$, where R$^d$ is defined analogously to R$^4$, or is —CH$_2$O—, —CH$_2$S—, —CH(Ar)O— or —CH(Ar)S—, Ar is an unsubstituted or substituted phenyl or napthyl radical of the formula

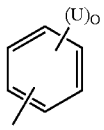 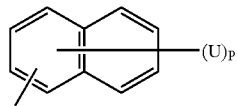

in which
- (U) are identical or different radicals which, independently of one another, are hydrogen, halogen, cyano, nitro, amino or C$_1$–C$_8$-haloalkyl, C$_1$–C$_8$-haloalkoxy, C$_1$–C$_8$-alkyl, C$_1$–C$_8$-alkoxy, mono-(C$_1$–C$_4$-alkyl)amino, di-(C$_1$–C$_4$-alkyl)amino, C$_1$–C$_8$-alkylthio or C$_1$–C$_8$-alkylsulfonyl, where each of the 8 last-mentioned radicals is unsubstituted or substituted by one or more identical or different substituents from the group consisting of halogen, C$_1$–C$_8$-haloalkoxy, nitro, cyano, hydroxyl, C$_1$–C$_8$-alkoxy, in which one or more CH$_2$ groups may be replaced by oxygen, C$_1$–C$_8$-alkylthio, C$_1$–C$_6$-alkylsulfinyl, C$_1$–C$_6$-alkylsulfonyl, C$_2$–C$_8$-alkenylthio, C$_2$–C$_8$-alkenyloxy, C$_2$–C$_8$-alkynyloxy, C$_3$–C$_7$-cycloalkyl, C$_3$–C$_7$-cycloalkoxy, mono- and di-(C$_1$–C$_4$-alkyl)amino and C$_1$–C$_8$-alkoxycarbonyl, and
- o is an integer from 1 to 5 and
- p is an integer from 1 to 7 or Ar is a monocyclic or bicyclic heteroaryl radical from the group consisting of furyl, thienyl, pyrrolyl, pyrazolyl, thiazolyl, oxazolyl, pyridinyl, pyrimidinyl, pyrazinyl, pyridazinyl and quinolinyl, each of which is unsubstituted or substituted by one or more of said radicals U, R is hydrogen or an aliphatic, aromatic, heteroaromatic, araliphatic or hetero araliphatic radical having I to 30 carbon atoms and, if desired, containing one or more functional groups, R$^T$ is a radical of the formula —CO—R, —CS—R, —NR$^f$R$^g$, —N=CR$^h$R$^i$ or SiR$^a$R$^b$R$^c$, where R is as defined above, and R$^f$, R$^g$, R$^h$ and R$^i$, independently of one another are hydrogen, C$_1$–C$_4$-alkyl, C$_2$–C$_4$-alkenyl, C$_2$–C$_4$-alkynyl, benzyl, phenyl or substituted phenyl, or R$^f$ and R$^g$ together with the nitrogen atom are a 5- or 6-membered heterocyclic ring which may contain up to 2 further heteroatoms from the group consisting of N, O and S, and which may be substituted by C$_1$–C$_4$-alkyl, and R$^a$, R$^b$ and R$^c$, independently of one another, are C$_1$–C$_4$-alkyl, C$_2$–C$_4$-alkenyl, C$_2$–C$_4$-alkynyl, phenyl or substituted phenyl, R$^4$ is hydrogen, C$_1$–C$_6$-alkyl, C$_2$–C$_6$-alkenyl, C$_2$–C$_6$-alkynyl, (C$_1$–C$_6$-alkyl)-carbonyl, where each of the 4 last-mentioned radicals is unsubstituted or substituted by one or more substituents from the group consisting of halogen, C$_1$–C$_8$-haloalkoxy, nitro, cyano, hydroxyl, C$_1$–C$_8$-alkoxy and C$_1$–C$_8$-alkoxy, in which one or more, preferably up to three, CH$_2$ groups which are not bonded directly to one another are replaced by oxygen, and C$_1$–C$_8$-alkylthio, C$_1$–C$_6$-alkylsulfonyl, C$_2$–C$_8$-alkenylthio, C$_2$–C$_8$-alkynylthio, C$_2$–C$_8$-alkenyloxy, C$_2$–C$_8$-alkynyloxy, C$_3$–C$_7$-cycloalkyl, C$_3$–C$_7$-cycloalkoxy and amino, mono- and di-(C$_1$–C$_4$-alkyl)amino, or are formyl, SiR$^a$R$^b$R$^c$, in which R$^a$, R$^b$ and R$^c$, independently of one another, are C$_1$–C$_4$-alkyl, C$_2$–C$_4$-alkenyl, C$_2$–C$_4$-alkynyl or substituted or unsubstituted phenyl, or are C$_3$–C$_8$-cycloalkyl, C$_3$–C$_8$-cycloalkenyl, heterocyclyl having 3 to 7 ring atoms, aryl, heteroaryl or arylcarbonyl, where each of the 6 last-mentioned radicals is unsubstituted or substituted by one or more radicals from the group consisting of C$_1$–C$_8$-alkyl, halogen, C$_1$–C$_8$-haloalkoxy, nitro, cyano, hydroxyl, C$_1$–C$_8$-alkoxy and C$_1$–C$_8$-alkoxy, in which one or more, CH$_2$ groups which are not bonded directly to one another are replaced by oxygen, and C$_1$–C$_8$-alkylthio, C$_1$–C$_6$-alkylsulfonly, C$_2$–C$_8$-alkenylthio, C$_2$–C$_8$-alkynylthio, C$_2$–C$_8$-alkenyloxy, C$_2$–C$_8$-alkynyloxy, C$_3$–C$_7$-cycloalkyl, C$_3$–C$_7$-cycloalkoxy, and amino, mono- and di-(C$_1$–C$_4$-alkyl)amino, or T is O, S, NR$^7$, NOR$^7$ or NO-acyl, Q is O or S, q is an integer from 0 to 4, i is a serial number which, if q is not equal to 0, adopts all integers from 1 to q, where q is as defined above, x$_i$ independently of one another, are O, S, NR$^7$ or N—(A$_i$—X$_i$—)$_q$—R, A$_i$ independently of one another, are unsubstituted or substituted C$_1$–C$_6$-alkylene, C$_2$–C$_6$-alkenylene, C$_2$–C$_6$-alkynylene, C$_3$–C$_6$-cycloalkylene, C$_3$–C$_6$-cycloalkenylene, heterocyclylene, arylene or heteroarylene, and R$^7$ independently of one another, are H, C$_1$–C$_4$-alkyl, C$_2$–C$_4$-alkenyl, C$_2$–C$_4$-alkynyl, C$_3$–C$_6$-cycloalkyl, C$_3$–C$_6$-cycloalkenyl, heterocyclyl, aryl or heteroaryl, except for (a) compounds of formula I in which
- R$^3$ is C$_1$–C$_4$-alkyl,
- Ar is phenyl, which is substituted by radicals U$^1$, U$^2$ and U$^3$ wherein U$^1$ is a radical selected from the group consisting of halogen, C$_1$–C$_4$-alkyl, C$_1$–C$_4$-alkoxy, CF$_3$ and C$_1$–C$_4$-alkylsulfonyl, and wherein U$^2$ and U$^3$ are identical or different radicals each selected from the group consisting of hydrogen, halogen, C$_1$–C$_4$-alkyl, C$_1$–C$_4$-alkoxy, CF$_3$ and C$_1$–C$_4$-alkylsulfonyl,
- X is an oxygen atom,
- R$^1$ is carboxy or (C$_1$–C$_4$-alkoxy)-carbonyl and R² is carboxy or (C₁–C₄-alkoxy)-carbonyl; or
(b) compounds of formula I in which
R³ is hydrogen,
Ar is phenyl, 2,4-dichlorophen-1-yl and 2,4,6-trichlorophen-1-yl, 3-methoxyphenyl, naphthyl, cumarinyl, 4-methyl-cumarinyl or 7-flavonyl,
X is an oxygen atom,
R¹ is —COOR,
R² is —COOR, and
R are identical or different radicals each selected from the group consisting of hydrogen, aryl, alkyl and aralkyl; or
(c) compounds of formula I in which
R³ is hydrogen,
Ar is 4-chlorophenyl,
X is an oxygen atom,
R¹ is —COOC₂H₅, and
R² is —COOC₂H₅; or
(d) compounds of formula I in which
R³ is hydrogen,
Ar is quinolin-8-yl,
X is a sulfur atom,
R¹ is —COOC₂H₅ and
R² is or —COOC₂H₅; or
(e) compounds of formula I in which
R³ is hydrogen, and
Ar is 3,5-dichloro-6-methyl-pyridin-2-yl,
X is oxygen atom, and
R¹ and R² are COOH or COOC₂H₅ or
(f) compounds of the formula 6-R¹-4-methoxy-pyrimidinyl-YCHR²COR³ in which
Y is oxygen or sulfur,
R¹ is halogen, alkoxy or haloalkoxy,
R² is alkoxycarbonyl, and
R³ is hydroxyl, unsubstituted or substituted alkoxy or phenoxy, alkenyloxy, alkynyloxy, alkylthio or alkenylthio; or
(g) 4,6-dimethylpyrimidin-2-yloxymalonic acid or diethyl 4,6-dimethylpyrimidin-2-yloxymalonate; or
(h) diethyl 2-methylthio-pyrimidin-5-yloxymalonate; or
(i) compound of formula (I) in which
R³ is hydrogen
Ar is pyrid-2-yl, 3-bromo-2-thienyl or 3-amino-5,6-dimethylpyrazin-2-yl,
X is a sulfur atom,
R¹ is ethoxycarbonyl and
R² is ethoxycarbonyl, or
(j) compound of formula (I) in which
R³ is hydrogen
Ar is 7-chloroquinolin-4-yl,
X is a group of the formula —NR$^d$— in which R$^d$ is 4-methoxyphenyl,
R¹ is ethoxycarbonyl and
R² is ethoxycarbonyl, or
(k) compound of formula (I) in which
R³ is methyl
Ar is 6-bromo-2-chloropyrid-3-yl or 2,6-dichloropyrid-3-yl or 3,5-dichloro-6-methylpyrid-2-yl or,
X is an oxygen atom,
R¹ is ethoxycarbonyl or carboxy and
R² is ethoxycarbonyl or carboxy, or
(l) compound of formula (I) in which
R³ is hydrogen
Ar is 3,5-dichloro-6-methylpyrid-2-yl,
X is an oxygen atom,
R¹ is ethoxycarbonyl or carboxy and
R² is ethoxycarbonyl or carboxy, or
(m) compound of formula (I) in which
R³ is hydrogen
Ar is 2,6-dimethoxypyrid-3-yl,
X is an group of the formula NH,
R¹ is ethoxycarbonyl and
R² is ethoxycarbonyl, or
(n) compound of formula (I) in which
R³ is methyl
Ar is pyrid-2-yl or,
X is a sulfur atom,
R¹ is ethoxycarbonyl and
R² is ethoxycarbonyl.

2. A compound as claimed in claim 1, wherein
Ar is an unsubstituted or substituted phenyl or naphthyl radical of the formula

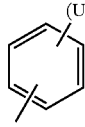 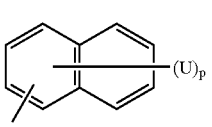

in which
(U) are identical or different radicals which, independently of one another, are hydrogen, halogen, cyano, nitro, amino or C₁–C₈-haloalkyl, C₁–C₈-haloalkoxy, C₁–C₈-alkyl, C₁–C,-alkoxy, mono-(C₁–C₄-alkyl) amino, di-(C₁–C₄-alkyl) amino, C₁–C₈-alkylthio or C₁–C₈-alkylsulfonyl, where each of the 8 last-mentioned radicals is unsubstituted or substituted by one or more identical or different substituents from the group consisting of halogen, C₁–C₈-haloalkoxy, nitro, cyano, hydroxyl, C₁–C₈-alkoxy, in which one or more CH₂ groups may be replaced by oxygen, C₁–C₈-alkylthio, C₁–C₆-alkylsulfinyl, C₁–C₆-alkylsulfonyl, C₂–C₈-alkenylthio, C₂–C₈-alkynylthio, C₂–C₈-alkenyloxy, C₂–C₈-alkynyloxy, C₃–C₇-cycloalkyl, C₃–C₇-cycloalkoxy, mono- and di-(C₁–C₄-alkyl) amino and C₁–C₈-alkoxycarbonyl, and
o is an integer from 1 to 5 and
p is an integer from 1 to 7 or
AE is a monocyclic or bicyclic heteroaryl radical from the group consisting of furyl, thienyl, pyrrolyl, pyrazolyl, thiazolyl, oxazolyl, pyridinyl, pyrimidinyl, pyrazinyl, pyridazinyl and quinolinyl, each of which is unsubstituted or substituted by one or more of said radicals U,
R is hydrogen, C₁–C₁₈-alkyl, C₃–C₁₂-cycloalkyl, C₂–C₈-alkenyl, C₂–C₈-alkynyl, heterocyclyl, phenyl or heteroaryl,
where each of the above C-containing radicals, independently of one another, is unsubstituted or substituted by one or more radicals from the group consisting of halogen, cyano, thio, nitro, hydroxyl, C₁–C₈-alkyl, the latter only in the case of cyclic radicals, C₁–C₈-haloalkyl, C₁–C₈-alkoxy, C₂–C₈-alkenyloxy, C₂–C₈-alkynyloxy, C₁–C₈-haloalkoxy, C₁–C₈-alkylthio, C₂–C₈-alkenylthio, C₂–C₈-alkynylthio, C₃–C₇-cycloalkyl, C₃–C₇-cycloalkoxy, radicals of the formulae —NR*R** and —CO—NR*R** and —O—CO—NR*R**, where R* and R** in the three last-mentioned radicals are, independently of one another, hydrogen, C₁–C₈-alkyl, C₂–C₇-alkenyl, C₂–C₈-alkynyl, benzyl, phenyl or substituted phenyl, or together with the nitrogen atom are a 3- to 8-membered heterocyclic ring which. may contain up to 2 further heteroatoms from the group consisting of N, O and S, and may be substituted by $C_1-C_4$-alkyl, and ($C_1-C_8$-alkoxy)carbonyl, ($C_1-C_8$-alkoxy)thiocarbonyl, ($C_2-C_8$-alkenyloxy)carbonyl, ($C_1-C_8$-alkylthio)carbonyl, ($C_2-C_8$-alkenylthio)carbonyl, ($C_2-C_8$-alkynylthio)carbonyl, ($C_2-C_8$-alkynyloxy)carbonyl, formyl, ($C_1-C_8$-alkyl)carbonyl, ($C_2-C_8$-alkenyl)carbonyl, ($C_2-C_8$alkynyl)carbonyl, $C_1-C_4$-alkylimino, $C_1-C_4$-alkoxyimino, ($C_1-C_8$-alkyl)carbonylamino, ($C_2-C_8$-alkenyl)carbonylamino, ($C_2-C_8$-alkynyl)carbonylamino, ($C_1-C_9$-alkoxy)carbonylamino, ($C_2-C_8$-alkenyloxy)carbonylamino, ($C_2-C_8$-alkynyloxy)carbonylamino, ($C_1-C_8$-alkyl)aminocarbonylamino, ($C_1-C_6$-alkyl)carbonyloxy, which is unsubstituted or substituted by halogen, $NO_2$, $C_1-C_4$-alkoxy or substituted or unsubstituted phenyl, ($C_2-C_6$-alkenyl)carbonyloxy, ($C_2-C_6$-alkynyl)carbonyloxy, ($C_1-C_8$-alkoxy)carbonyloxy, ($C_2-C_8$-alkenyloxy)-carbonyloxy, ($C_2-C_8$-alkynyloxy)carbonyloxy, $C_1-C_8$-alkylsulfonyl, phenyl, phenyl-$C_1-C_6$-alkoxy, phenyl-($C_1-C_6$-alkoxy)carbonyl, phenoxy, phenoxy-$C_1-C_6$-alkoxy, phenoxy-($C_1-C_6$-alkoxy)-carbonyl, phenoxycarbonyl, phenylcarbonyloxy, phenylcarbonylamino, phenyl-($C_1-C_6$-alkyl)-carbonylamino and phenyl-($C_1-C_6$-alkyl)-carbonyloxy, where the 11 last-mentioned radicals are unsubstituted or substituted on the phenyl ring by one or more radicals from the group consisting of halogen, $C_1-C_4$-alkyl, $C_1-C_4$-alkoxy, $C_1-C_4$-haloalkyl, $C_1-C_4$-haloalkoxy and nitro, and radicals of the formulae —$SiR'_3$, —O—$SiR'_3$, $(R')_3SiC_1-C_6$-alkoxy, —CO—O—$NR'_2$, —O—N=$CR'_2$, —N=$CR'_2$, —O—$NR'_2$, —CH$(OR')_2$, and —O—$(CH_2)_m$—CH$(OR')_2$, in which the R' in said formulae are, independently of one another, hydrogen, $C_1-C_4$-alkyl or phenyl, which is unsubstituted or monosubstituted or polysubstituted by radicals from the group consisting of halogen, $C_1-C_4$-alkyl, $C_1-C_4$-alkoxy, $C_1-C_4$-haloalkyl, $C_1-C_4$-haloalkoxy and nitro, or in pairs are a $C_2-C_6$-alkylene chain and m=0 to 6, or a substituted alkoxy radical of the formula R"O—CHR'''CH(OR")—$C_1-C_6$-alkyl, in which the R", independently of one another, are $C_1-C_4$-alkyl or together are a $C_1-C_6$-alkylene group, and R''' is hydrogen or $C_1-C_4$-alkyl.

3. A compound as claimed in claim 1, wherein

R is hydrogen, $C_1-C_8$-alkyl, $C_5-C_6$-cycloalkyl, $C_2-C_8$-alkenyl or $C_2-C_8$-alkynyl, where each of the 4 last-mentioned radicals, independently of one another, are unsubstituted or substituted by one or more radicals from the group consisting of halogen, cyano, nitro, $C_1-C_4$-alkoxy, $C_2-C_4$-alkenyloxy, $C_2-C_4$-alkynyloxy, $C_5-C_6$-cycloalkyl, $C_5-C_6$-cycloalkoxy, mono- and di—($C_1-C_4$-alkyl)amino, radicals of the formulae —$SiR'_3$, —O—N=$CR'_2$, —N=$CR'_2$, in which the R' in said formulae are, independently of one another, hydrogen, $C_1-C_2$-alkyl or phenyl or in pairs are a $C_2-C_5$-alkylene chain, $R^T$ is —CO—R, —$NR^fR^g$ or —N=$CR^hR^i$, in which $R^f$ and $R^g$, independently of one another, are H, $C_1-C_2$-alkyl, benzyl or phenyl or together with the nitrogen atom are pyrrolidin-1-yl, piperidin-1-yl, morpholin-4-yl, piperazin-1-yl or imidazol-1-yl, and $R^h$ and $R^i$, independently of one another, are H, $C_1-C_2$-alkyl, benzyl or phenyl, $R^4$ and $R^5$ are identical or different and, independently of one another, are hydrogen, $C_1-C_4$-alkyl, $C_2-C_4$-alkenyl, $C_2-C_4$-alkynyl, $C_5-C_6$-cycloalkyl or $C_5-C_6$-cycloalkenyl, $R^6$ is hydrogen, $C_1-C_6$-alkyl, phenyl, benzyl, hydroxyl, NH—CO—$NH_2$, —NH-aryl or $C_1-C_4$-alkoxy, T is O, S or $NR^7$, Q is O or S, q is an integer from 0 to 4, i is a serial number which, if q is not equal to 0, adopts all integers from 1 to q, $X_i$ independently of one another, are O, S, $NR^7$ or N—$(A_i—X_i—)_q$—R, $A_i$ independently of one another, are unsubstituted, or substituted $C_1-C_4$-alkylene, $C_2-C_4$-alkenylene or $C_5-C_6$-cycloalkylene, $R^7$ independently of one another, are H, $C_1-C_4$-alkyl, $C_2-C_4$-alkenyl, $C_2-C_4$-alkynyl or $C_5-C_6$-cycloalkyl.

4. A compound as claimed in claim 1, wherein $R^1$ and $R^2$, independently of one another, are radicals of the formula $$-\overset{O}{\underset{\|}{C}}-Q-(A_iX_i)_{\overline{q}}-R \text{ or CN.}$$

5. A compound as claimed in claim 1 or a salt thereof, wherein

Ar is a monocyclic or bicyclic heteroaryl radical selected from the group consisting of furyl, thienyl, pyrrolyl, pyrazolyl, thiazolyl, oxazolyl, pyridinyl, pyrimidinyl, pyrazinyl, pyridazinyl and quinolinyl, each of which is unsubstituted or substituted with one or moreradicals selected from the group consisting of $U^1$, $U^2$ and $U^3$, except for a compound of formula I in which Ar=quinolin-8yl, X=S, $R^1$=$COOC_2H_5$, $R^2$=$COOC_2H_5$ or $COCH_3$ and $R^3$=H.

6. A compound as claimed in claim 1 or a salt thereof, wherein

Ar is a monocyclic or bicyclic heteroaryl radical selected from the group consisting of furyl, thienyl, pyrrolyl, pyrazolyl, thiazolyl, oxazolyl, pyridinyl, pyrimidinyl, pyrazinyl, pyridazinyl and quinolinyl, each of which is unsubstituted or substituted with one or more radicals selected from the groups consisting of $U^1$, $U^2$ and $U^3$, and X is an oxygen atom.

7. A compound as claimed in claim 6 or a salt thereof, wherein

Ar is pyridinyl which is unsubstituted or substituted with one or more radicals selected from the group consisting of $U^1$, $U^2$ and $U^3$.

8. A compound as claimed in claim 6 or a salt thereof, wherein

Ar is quinolinyl which is unsubstituted or substituted with one or more radicals selected from the group consisting of $U^1$, $U^2$ and $U^3$.

9. A compound as claimed in claim 6 or a salt thereof, wherein

Ar is pyrimidinyl which is unsubstituted or substituted with one or more radicals selected from the group consisting of $U^1$, $U^2$ and $U^3$.

10. A compound as claimed in claim 6 or a salt thereof, wherein

Ar is triazinyl which is unsubstituted or substituted with one or more radicals selected from the group consisting of $U^1$, $U^2$ and $U^3$.

11. A compound of formula (I) as claimed in claim 1, wherein $R^2$ is a radical of the formula

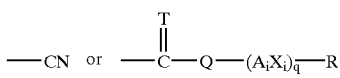

in which R, T, Q, A, X, I and q are defined in formula (I).

12. A compound of the formula (I) as claimed in claim 1, wherein $R^1$ and $R^2$ independently of one another are a radical of the formula

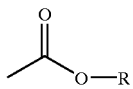

in which R is as defined in formula (I) and X is oxygen.

13. A process for the preparation of a compound of the formula I as claimed in claim 1, which comprises a) reacting a compound of the formula Ar—(X)$_n$—H, in which Ar and X are as defined under formula I and n=1, with a compound of the formula II

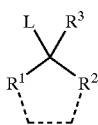

(II)

in which
L is a leaving group and
$R^1$, $R^2$ and $R^3$ are as defined under said formula I, or b) reacting a compound of the formula Ar—W with a compound of the formula III

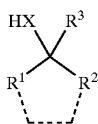

(III)

where
W is a leaving group and
Ar, X, $R^1$, $R^2$ and $R^3$ are as defined under said formula I, or c) reacting a compound of the formula AR—X—W with a compound of the formula IV

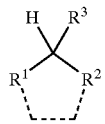

(IV)

where
W is a leaving group and
Ar, X, $R^1$, $R^2$ and $R^3$ are as defined under formula I, or d) transesterifying an aryl- or heteroaryloxy-carboxylic acid derivative of the formula V

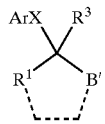

(V)

in which
Ar, X, $R^1$ and $R^3$ are as defined under formula I, and
B' is a group of the formulae

are bonded to one another and together are a group of the formula —CO—Q$^1$—D—Q$^2$—CO—, where T, Q, A$_i$, X$_i$, q, R, R$^T$ Q$^1$, Q$^2$ and D are defined analogously to the radicals of the same names in formula I, with alcohols or mercaptans.

* * * * *